(12) United States Patent
Gavai et al.

(10) Patent No.: US 7,064,203 B2
(45) Date of Patent: Jun. 20, 2006

(54) DI-SUBSTITUTED PYRROLOTRIAZINE COMPOUNDS

(75) Inventors: Ashvinikumar V. Gavai, Princeton Junction, NJ (US); Wen-Ching Han, Newtown, PA (US); Ping Chen, Belle Mead, NJ (US); Edward H. Ruediger, Greenfield Park (CA); Harold Mastalerz, Guilford, CT (US); Brian E. Fink, Princeton Junction, NJ (US); Derek J. Norris, Pennington, NJ (US)

(73) Assignee: Bristol Myers Squibb Company, Princeton, NJ (US)

( * ) Notice: Subject to any disclaimer, the term of this patent is extended or adjusted under 35 U.S.C. 154(b) by 47 days.

(21) Appl. No.: 11/019,899

(22) Filed: Dec. 22, 2004

(65) Prior Publication Data

US 2005/0197339 A1     Sep. 8, 2005

Related U.S. Application Data

(60) Provisional application No. 60/533,361, filed on Dec. 29, 2003.

(51) Int. Cl.
*C07D 487/04* (2006.01)
*A61K 31/53* (2006.01)
*A61P 19/02* (2006.01)

(52) U.S. Cl. ...................... 544/183; 514/243
(58) Field of Classification Search ............... 544/183; 514/243
See application file for complete search history.

(56) References Cited

U.S. PATENT DOCUMENTS

| | | |
|---|---|---|
| 6,670,357 B1 | 12/2003 | Leftheris et al. |
| 6,787,545 B1 | 9/2004 | Ohtani et al. |
| 6,867,300 B1 | 3/2005 | Godfrey, Jr. et al. |
| 6,869,952 B1 | 3/2005 | Bhide et al. |
| 6,908,916 B1 | 6/2005 | Mastalerz et al. |
| 6,916,815 B1 | 7/2005 | Vite et al. |
| 2003/0232831 A1 | 12/2003 | Dyckman et al. |
| 2003/0232832 A1 | 12/2003 | Lombardo et al. |
| 2004/0063707 A1 | 4/2004 | Bhide et al. |
| 2004/0063708 A1 | 4/2004 | Bhide et al. |
| 2004/0077858 A1 | 4/2004 | Bhide et al. |
| 2004/0229877 A1 | 11/2004 | Leftheris et al. |

FOREIGN PATENT DOCUMENTS

| | | |
|---|---|---|
| EP | 0 713 876 | 5/1996 |
| WO | WO 98/08847 | 3/1998 |
| WO | WO 00/71129 | 11/2000 |
| WO | WO 02/40486 | 5/2002 |
| WO | WO 03/090912 | 11/2003 |
| WO | WO 2004/009784 | 1/2004 |

OTHER PUBLICATIONS

Cecil Textbook of Medicine, edited by Bennet, J.C., and Plum F., 20th edition, vol. 1, 1004-1010, 1996.*
Wolft Manfred E. "Burger's Medicinal Chemistry, 5ed, Part 1", John Wiley & Sons, 1995, pp. 975-977.*
Banker, G.S. et al, "Modern Pharmaceutices, 3ed.", Marcel Dekker, New York. 1996, pp. 451 and 596.*
Tsi-Ping et al., TIPS 16: 5766, 1995.*
U.S. Appl. No. 11/008,719, filed Dec. 9, 2004, Swaminathan et al.
U.S. Appl. No. 11/019,901, filed Dec. 22, 2004, Fink et al.
Ewald, H. et al., "Reaktionen von 1,2,4-Triazinen mit Acetylendicarbonsäure-dimethylester", Liebigs Ann. Chem., pp. 1718-1724 (1977).
Hunt, J.T. et al., "Discovery of the Pyrrolo[2,1-f][1,2,4]triazine Nucleus as a New Kinase Inhibitor Template", J. Med. Chem., vol. 47, No. 16, pp. 4054-4059 (2004).
Migliara, O. et al., "Synthesis of a New Bridgehead Nitrogen Heterocyclic System. Pyrrolo[2,1-f]-1,2,4-triazine Derivatives", J. Heterocyclic Chem., vol. 16, pp. 833-834 (1979).
Neunhoeffer, H. et al., "Cycloadditionen mit Methoxy- und Dialkylamino-1,2,4-triazinen", Liebigs Ann. Chem., pp. 1413-1420 (1977).
Patil, S.A. et al., "Synthesis of Pyrrolo[2,1-f][1,2,4]triazine Congeners of Nucleic Acid Purines via the N-Amination of 2-Substituted Pyrroles", J. Heterocyclic Chem., vol. 31, pp. 781-786 (1994).
Quintela, J.M. et al., "A Ready One-pot Preparation for Pyrrolo[2,1-f][1,2,4]triazine and Pyrazolo[5,1-c]pyrimido[4,5-e]-[1,2,4]triazine Derivatives", Tetrahedron, vol. 52, No. 8, pp. 3037-3048 (1996).
U.S. Appl. No. 60/620,784, filed Oct. 21, 2004, Gavai et al.
U.S. Appl. No. 11/152,650, filed Jun. 14, 2005, Cai et al.
U.S. Appl. No. 11/157,460, filed Jun. 21, 2005, Gavai et al.

* cited by examiner

*Primary Examiner*—Venkataraman Balasubramanian
(74) *Attorney, Agent, or Firm*—Elliott Korsen

(57) ABSTRACT

The present invention provides compounds of formula I

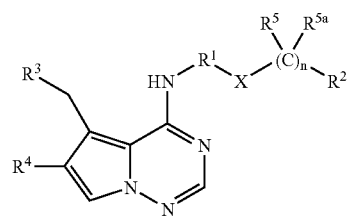

and pharmaceutically acceptable salts thereof.

The compounds of the invention inhibit tyrosine kinase activity of growth factor receptors such as HER1, HER2 and HER4 thereby making them useful as antiproliferative agents for the treatment of cancer and other diseases.

6 Claims, No Drawings

DI-SUBSTITUTED PYRROLOTRIAZINE COMPOUNDS

This application claims the priority benefit of U.S. Provisional Application No. 60/533,361 filed Dec. 29, 2003, which is incorporated herein by reference in its entirety.

FIELD OF THE INVENTION

This invention relates to compounds that inhibit the tyrosine kinase activity of growth factor receptors such as HER1, HER2, and HER4 thereby making them useful as anti-cancer agents. The compounds are also useful in the treatment of diseases, other than cancer, which are associated with signal transduction pathways operating through growth factor receptors such as HER1, HER2 and HER4.

BACKGROUND OF THE INVENTION

Receptor tyrosine kinases (RTKs) are important in the transmission of biochemical signals across the plasma membrane of cells. These transmembrane molecules characteristically consist of an extracellular ligand-binding domain connected through a segment in the plasma membrane to an intracellular tyrosine kinase domain.

The human epidermal growth factor receptor (HER) family consists of four distinct receptor tyrosine kinases referred to HER1, HER2, HER3, and HER4. These kinases are also referred to as erbB1, erbB2, etc. HER1 is also commonly referred to as the epidermal growth factor (EGF) receptor. With the exception of HER3, these receptors have intrinsic protein kinase activity that is specific for tyrosine residues of phosphoacceptor proteins. The HER kinases are expressed in most epithelial cells as well as tumor cells of epithelial origin. They are also often expressed in tumor cells of mesenchymal origin such as sarcomas or rhabdomybsarcomas. RTKs such as HER1 and HER2 are involved in cell proliferation and are associated with diseases such as psoriasis and cancer. Disruption of signal transduction by inhibition of these kinases would have an antiproliferative and therapeutic effect.

The enzymatic activity of receptor tyrosine kinases can be stimulated by either overexpression, or by ligand-mediated dimerization. The formation of homodimers as well as heterodimers has been demonstrated for the HER receptor family. An example of homodimerization is the dimerization of HER1 (EGF receptor) by one of the EGF family of ligands (which includes EGF, transforming growth factor alpha, betacellulin, heparin-binding EGF, and epiregulin). Heterodimerization among the four HER receptor kinases can be promoted by binding to members of the heregulin (also referred to neuregulin) family of ligands. Such heterodimerization as involving HER2 and HER3, or a HER3/HER4 combination, results in a significant stimulation of the tyrosine kinase activity of the receptor dimers even though one of the receptors (HER3) is enzymatically inert. The kinase activity of HER2 has been shown to be activated also by virtue of overexpression of the receptor alone in a variety of cell types. Activation of receptor homodimers and heterodimers results in phosphorylation of tyrosine residues on the receptors and on other intracellular proteins. This is followed by the activation of intracellular signaling pathways such as those involving the microtubule associated protein kinase (MAP kinase) and the phosphatidylinositol 3-kinase (PI3 kinase). Activation of these pathways have been shown to lead to cell proliferation and the inhibition of apoptosis. Inhibition of HER kinase signaling has been shown to inhibit cell proliferation and survival.

SUMMARY OF THE INVENTION

The compounds of the invention inhibit the tyrosine kinase activity of growth factor receptors such as HER1, HER2, and HER4 and as such, can be used to treat diseases that are associated with signal transduction pathways operating through growth factor receptors. For example the compounds of the instant invention can be used as antiproliferatives and anticancer agents. More specifically, the invention comprises a compound of formula I

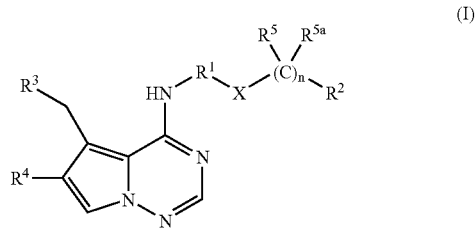

wherein the symbols have the following meanings and are, for each occurrence, independently selected:

$R^1$ and $R^2$ are independently aryl, substituted aryl, heteroaryl, substituted heteroaryl, heterocyclo or substituted heterocyclo;

$R^3$ and $R^4$ are independently hydrogen, alkyl, substituted alkyl, halogen, alkoxy, substituted alkoxy, aryl, substituted aryl, heteroaryl, substituted heteroaryl, heterocyclo, substituted heterocyclo, alkylheterocyclo, substituted alkylheterocyclo, —O-heterocyclo or —NHCOOalkylheterocyclo;

$R^5$ and $R^{5a}$ are hydrogen, alkyl, substituted alkyl or halogen,

X is —O— or $NR^5$;

n is 1 or 2;

or a pharmaceutically acceptable salt, solvate, prodrug or isomer thereof.

Also provided for is a method for treating proliferative diseases, comprising administering to a mammalian species in need thereof, a therapeutically effective amount of a compound of formula I.

DETAILED DESCRIPTION OF THE INVENTION

The present invention provides for compounds of formula I, pharmaceutical compositions employing such compounds and for methods of using such compounds.

In accordance with the present invention, compounds of formula I

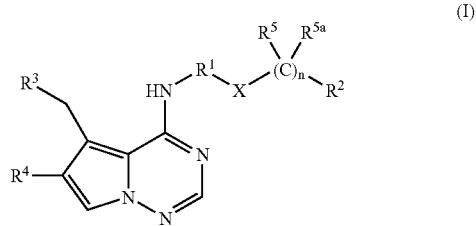

wherein the symbols have the following meanings and are, for each occurrence, independently selected:

$R^1$ and $R^2$ are independently aryl, substituted aryl, heteroaryl, substituted heteroaryl, heterocyclo or substituted heterocyclo;

$R^3$ and $R^4$ are independently hydrogen, alkyl, substituted alkyl, halogen, alkoxy, substituted alkoxy, aryl, substituted aryl, heteroaryl, substituted heteroaryl, heterocyclo, substituted heterocyclo, alkylheterocyclo, substituted alkylheterocyclo, —O-heterocyclo or —NHCOOalkylheterocyclo;

$R^5$ and $R^{5a}$ are hydrogen, alkyl, substituted alkyl or halogen,

X is —O— or $NR^5$;

n is 1 or 2;

or a pharmaceutically acceptable salt, solvate, prodrug or isomer thereof, inhibit the tyrosine kinase activity of growth factor receptors such as HER2.

Preferred compounds of the invention are those wherein X is —O—;

$R^1$ and $R^2$ are independently aryl, substituted aryl, heteroaryl or substituted heteroaryl; and $R^5$ and $R^{5a}$ are hydrogen or lower alkyl.

In another preferred embodiment, $R^4$, $R^5$ and $R^{5a}$ are hydrogen.

More preferred $R^1$ and $R^2$ substitutents include oxazolyl, thienyl, pyridinyl, thiazolyl, pyrazinyl, and phenyl, all of which may be suitably substituted with one or more substitutents.

More preferred $R^3$ and $R^4$ include benzyl, imidazolyl-ethyl, (methyl-imidazolyl)-ethyl, piperidinyl-ethyl, pyridinyl-propyl, pyridinyl-methyl, morpholinyl-ethyl, (methyl-imidazolyl)-methyl, pyridinyl-ethyl, amino-piperidinyl-methyl, 4-amino-1-methyl-piperidin-3-ol, (methyl-piperazinyl)-ethyl, pyridinyl-ethyl, (methyl-piperidinyl)-ethyl, (methyl-imidazolyl)-propyl, (methyl-piperidinyl)-methyl, (methyl-piperazinyl)-propyl, diisopropylamino-ethyl, piperidinyl-propyl, dimethylamino-ethyl, dimethylamino-propyl, [(trifluoro-acetyl)-piperidinyl]-propyl, piperidinyl-ethyl, piperazinyl-ethyl, piperazinyl-propyl, pyrrolidinyl-ethyl, triazolyl-ethyl, triazolyl-propyl, (dimethylamino-ethoxy)-ethyl, imidazolyl-propyl, [(trifluoro-acetyl)-piperidinyl]-propyl, (piperazinyl-ethoxy)-ethyl, [(trifluoro-acetyl)-piperazinyl]-propyl, [(trifluoro-acetyl)-piperazinyl]-ethyl, piperidinyl-methyl, pyrazolyl-ethyl, (amino-ethoxy)-ethyl, (methoxy-ethoxy)-ethyl, pyrazolyl-propyl, [(methoxy-ethyl)-methyl-amino]-ethyl, morpholinyl-propyl, (cyanomethyl-piperazinyl)-ethyl, [(cyano-ethyl)-methyl-amino]-ethyl, [(methoxy-ethyl)-piperidinyl]-methyl, [(methoxy-ethyl)-piperidinyl]-ethyl, [(fluoro-ethyl)-methyl-amino]-ethyl, [(fluoro-ethyl)-methyl-amino]-propyl, (methyl-piperidinyl)-propyl, [(methanesulfonyl-ethyl)-piperazinyl]-ethyl, [(cyano-ethyl)-piperazinyl]-ethyl, [(methoxy-ethyl)-piperazinyl]-ethyl, [(methoxy-ethyl)-methyl-amino]-propyl, (cyanomethyl-methyl-amino)-propyl, (cyanomethyl-methyl-amino)-ethyl, [(methanesulfonyl-ethyl)-methyl-amino]-propyl, (difluoro-piperidinyl)-propyl, (difluoro-piperidinyl)-ethyl, [(cyano-ethyl)-methyl-amino]-propyl, [(methanesulfonyl-ethyl)-methyl-amino]-ethyl, [(trifluoro-ethyl)-piperazinyl]-ethyl, [cyanomethyl-(methanesulfonyl-ethyl)-amino]-propyl, [cyanomethyl-(methanesulfonyl-ethyl)-amino]-ethyl, (cyanomethyl-piperazinyl)-propyl, [(methanesulfonyl-ethyl)-piperazinyl]-propyl, [(cyano-ethyl)-piperazinyl]-propyl, [(trifluoro-ethyl)-piperazinyl]-propyl, (methanesulfonyl-ethyl-amino)-ethyl, [(cyano-ethyl)-piperidinyl]-methyl, (cyanomethyl-piperidinyl)-methyl, (hydroxy-piperidinyl)-propyl, [(methanesulfonyl-ethyl)-piperidinyl]-methyl, piperidinyl-methyl, piperidinyl, imidazolyl-propyl, 1-methyl-[1,4]-diazepan-6-ol, methanesulfonyl-propyl, (methanesulfonyl-ethyl-amino)-propyl, pyrrolidinyl-methyl, methanesulfonyl-ethyl, (cyanomethyl-amino)-ethyl, (cyanomethyl-amino)-propyl, (dioxo-thiomorpholinyl)-propyl, (oxo-piperidinyl)-propyl, [(difluoro-ethyl)-methyl-amino]-ethyl, morpholinyl-methyl, (hydroxy-pyrrolidinyl)-propyl, (hydroxy-piperidinyl)-propyl, pyrrolidinyl-methyl, (hydroxy-pyrrolidinyl)-propyl, methyl-piperidinyl, (methyl-pyrrolidinyl)-methyl, morpholinyl-methyl, pyrrolidinyl-methyl, (methyl-tetrahydropyridinyl)-methyl, (cyano-ethyl)-piperidinyl, azetidinyl, (methanesulfonyl-ethyl)-piperidinyl, (cyano-methyl)-piperidinyl, isopropyl-piperidinyl, propyl-piperidinyl, acetyl-piperidinyl, ethyl-piperidinyl, allyl-piperidinyl, tetrahydropyranyl, (hydroxy-ethyl)-piperidinyl, (methyl-pyrrolidinyl)-methyl, (methoxyethyl)-piperidinyl, piperidinyl, (methoxy-ethyl)-azetidinyl, (methoxy-methoxymethyl-ethyl)-piperidinyl, (methoxy-acetyl)-piperidinyl, methoxycarbonyl-piperidnyl, (hydroxy-acetyl)-piperidinyl, piperidine-carboxylic acid-acetoxy-ethyl, piperidine-carboxylic acid-acetoxy-methyl-ethyl, hydroxy-piperidinyl, amino-cyclohexyl, piperidinyl, piperidine-carboxylic acid-methyl-oxo-dioxolylmethyl, hydroxymethyl-piperidinyl, (aminomethyl)-cyclohexyl, amino-methyl-cyclohexyl, hydroxy-piperidinyl-methyl, morpholinyl, amino-cyclohexyl, hydroxymethyl-piperidinyl, tetrahydro-pyranyl, methanesulfonyl-propyl, amino-methyl-propyl, amino-cyclohexyl, amino-methyl-cyclohexyl, (hydroxy-piperidinyl)-propyl, piperidinyl, amino-propyl, morpholinyl-methyl, piperidinyl, (tert-butoxycarbonyl-morpholinyl)-methyl, benzyl, imidazolyl-ethyl, piperidinyl-ethyl, methoxyethyl, (diethylamino)-(methoxyethyl), pyrrolidinyl-ethyl, acetamide and methyl.

Particularly preferred $R^1$ and $R^2$ substituents include aryl or heteroaryl optionally substituted with one or more substituents selected from the group consisting of hydrogen, halogen, alkyl, —CN, —$NH_2$, alkoxy, aryloxy, substituted aryloxy, —$CONR^4R^5$, —NHCOalkyl, —$CF_3$ and —$OCF_3$.

Preferred compounds of the invention include, without limitation, the following

[5-(4-Amino-piperidin-1-ylmethyl)-pyrrolo[2,1-f][1,2,4]triazin-4-yl]-[3-chloro-4-(pyridin-2-ylmethoxy)-phenyl]-amine;

[5-(4-Amino-piperidin-1-ylmethyl)-pyrrolo[2,1-f][1,2,4]triazin-4-yl]-[3-chloro-4-(pyridin-3-ylmethoxy)-phenyl]-amine;

[5-(4-Amino-piperidin-1-ylmethyl)-pyrrolo[2,1-f][1,2,4]triazin-4-yl]-[3-chloro-4-(3-fluoro-benzyloxy)-phenyl]-amine;

5-[[5-[(4-Amino-1-piperidinyl)methyl]pyrrolo[2,1-f][1,2,4]triazin-4-yl]amino]-2-[(3-fluorophenyl)methoxy]benzonitrile;

5-[(4-Amino-1-piperidinyl)methyl]-N-[3-chloro-4-(pyrazinylmethoxy)-phenyl]pyrrolo[2,1-f][1,2,4]triazin-4-amine;

5-[[(3R,4S)-rel-4-Amino-3-methyl-1-piperidinyl]methyl]-N-[3-chloro-4-(2-pyridinylmethoxy)phenyl]pyrrolo[2,1-f][1,2,4]triazin-4-amine;

5-[(4-Amino-1-piperidinyl)methyl]-N-[3-chloro-4-[(1-oxido-2-pyridinyl)methoxy]phenyl]pyrrolo[2,1-f][1,2,4]triazin-4-amine, and trans-4-Amino-1-{4-[3-chloro-4-(pyridin-2-ylmethoxy)-phenylamino]-pyrrolo[2,1-f][1,2,4]triazin-5-yl-methyl}-piperidin-3-ol.

Preferred compounds of the instant invention exhibit $IC_{50}$ values of less than 5 µM in one or more of HER1, HER2 and HER4 assays. More preferred are compounds have less than 1 µM assay activity. Even more preferred are compounds having less than 0.1 µM assay activity.

The following are definitions of terms that may be used in the present specification. The initial definition provided for a group or term herein applies to that group or term throughout the present specification individually or as part of another group, unless otherwise indicated.

The term "alkyl" refers to straight or branched chain unsubstituted hydrocarbon groups of 1 to 20 carbon atoms, preferably 1 to 7 carbon atoms. The expression "lower alkyl" refers to unsubstituted alkyl groups of 1 to 4 carbon atoms.

The term "substituted alkyl" refers to an alkyl group substituted by, for example, one to four substituents, such as, halo, hydroxy, alkoxy, oxo, alkanoyl, aryloxy, alkanoyloxy, amino, alkylamino, arylamino, aralkylamino, disubstituted amines in which the 2 amino substituents are selected from alkyl, aryl or aralkyl; alkanoylamino, aroylamino, aralkanoylamino, substituted alkanoylamino, substituted arylamino, substituted aralkanoylamino, thiol, alkylthio, arylthio, aralkylthio, alkylthiono, arylthiono, aralkylthiono, alkylsulfonyl, arylsulfonyl, aralkylsulfonyl, sulfonamido, e.g. $SO_2NH_2$, substituted sulfonamido, nitro, cyano, carboxy, carbamyl, e.g. $CONH_2$, substituted carbamyl e.g. CONHalkyl, CONHaryl, CONHaralkyl or cases where there are two substituents on the nitrogen selected from alkyl, aryl or aralkyl; alkoxycarbonyl, aryl, substituted aryl, guanidino, heterocyclo, e.g., indolyl, imidazolyl, furyl, thienyl, thiazolyl, pyrrolidyl, pyridyl, pyrimidyl, pyrrolidinyl, piperidinyl, morpholinyl, piperazinyl, homopiperazinyl and the like, and substituted heterocyclo. Where noted above where the substituent is further substituted it will be with alkyl, alkoxy, aryl or aralkyl.

The term "halogen" or "halo" refers to fluorine, chlorine, bromine and iodine.

The term "aryl" refers to monocyclic or bicyclic aromatic hydrocarbon groups having 6 to 12 carbon atoms in the ring portion, such as phenyl, naphthyl, biphenyl and diphenyl groups, each of which may be substituted.

The term "aralkyl" refers to an aryl or a substituted aryl group bonded directly through an alkyl group, such as benzyl.

The term "substituted aryl" refers to an aryl group substituted by, for example, one to four substituents such as alkyl, substituted alkyl, alkenyl, substituted alkenyl, alkynyl, substituted alkynyl, aryl, substituted aryl, aralkyl, halo, trifluoromethoxy, trifluoromethyl, hydroxy, alkoxy, alkanoyl, alkanoyloxy, aryloxy, aralkyloxy, amino, alkylamino, arylamino, aralkylamino, dialkylamino, alkanoylamino, thiol, alkylthio, ureido, nitro, cyano, carboxy, carboxyalkyl, carbamyl, alkoxycarbonyl, alkylthiono, arylthiono, arylsulfonylamine, sulfonic acid, alkysulfonyl, sulfonamido, aryloxy and the like. The substituent may be further substituted by hydroxy, halo, alkyl, alkoxy, alkenyl, alkynyl, aryl or aralkyl.

The term "heteroaryl" refers to an optionally substituted, aromatic group for example, which is a 4 to 7 membered monocyclic, 7 to 11 membered bicyclic, or 10 to 15 membered tricyclic ring system, which has at least one heteroatom and at least one carbon atom-containing ring, for example, pyridine, tetrazole, indazole.

The term "alkenyl" refers to straight or branched chain hydrocarbon groups of 2 to 20 carbon atoms, preferably 2 to 15 carbon atoms, and most preferably 2 to 8 carbon atoms, having one to four double bonds.

The term "substituted alkenyl" refers to an alkenyl group substituted by, for example, one to two substituents, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino, indolyl, imidazolyl, furyl, thienyl, thiazolyl, pyrrolidyl, pyridyl, pyrimidyl and the like.

The term "alkynyl" refers to straight or branched chain hydrocarbon groups of 2 to 20 carbon atoms, preferably 2 to 15 carbon atoms, and most preferably 2 to 8 carbon atoms, having one to four triple bonds.

The term "substituted alkynyl" refers to an alkynyl group substituted by, for example, a substituent, such as, halo, hydroxy, alkoxy, alkanoyl, alkanoyloxy, amino, alkylamino, dialkylamino, alkanoylamino, thiol, alkylthio, alkylthiono, alkylsulfonyl, sulfonamido, nitro, cyano, carboxy, carbamyl, substituted carbamyl, guanidino and heterocyclo, e.g. imidazolyl, furyl, thienyl, thiazolyl, pyrrolidyl, pyridyl, pyrimidyl and the like.

The term "cycloalkyl" refers to an optionally substituted, saturated cyclic hydrocarbon ring systems, preferably containing 1 to 3 rings and 3 to 7 carbons per ring which may be further fused with an unsaturated $C_3$–$C_7$ carbocylic ring. Exemplary groups include cyclopropyl, cyclobutyl, cyclopentyl, cyclohexyl, cycloheptyl, cycloctyl, cyclodecyl, cyclododecyl, and adamantyl. Exemplary substituents include one or more alkyl groups as described above, or one or more groups described above as alkyl substituents.

The terms "heterocycle", "heterocyclic" and "heterocyclo" refer to an optionally substituted, fully saturated or unsaturated, aromatic or nonaromatic cyclic group, for example, which is a 4 to 7 membered monocyclic, 7 to 11 membered bicyclic, or 10 to 15 membered tricyclic ring system, which has at least one heteroatom in at least one carbon atom-containing ring. Each ring of the heterocyclic group containing a heteroatom may have 1, 2 or 3 heteroatoms selected from nitrogen atoms, oxygen atoms and sulfur atoms, where the nitrogen and sulfur heteroatoms may also optionally be oxidized and the nitrogen heteroatoms may also optionally be quaternized. The heterocyclic group may be attached at any heteroatom or carbon atom.

Exemplary monocyclic heterocyclic groups include pyrrolidinyl, pyrrolyl, indolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, homopiperazinyl, 2-oxohomopiperazinyl, 2-oxopyrrolidinyl, 2-oxazepinyl, azepinyl, 4-piperidonyl, pyridyl, N-oxo-pyridyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, dioxanyl, isothiazolidinyl, thietanyl, thiiranyl, triazinyl, and triazolyl, and the like.

Exemplary bicyclic heterocyclic groups include 2,3-dihydro-2-oxo-1H-indolyl, benzothiazolyl, benzoxazolyl, benzothienyl, quinuclidinyl, quinolinyl, quinolinyl-N-oxide, tetrahydroisoquinolinyl, isoquinolinyl, benzimidazolyl, benzopyranyl, indolizinyl, benzofuryl, chromonyl, coumarinyl, cinnolinyl, quinoxalinyl, indazolyl, pyrrolopyridyl, furopyridinyl (such as furo[2,3-c]pyridinyl, furo[3,1-b]pyridinyl, or furo[2,3-b]pyridinyl), dihydroisoindolyl, dihydroquinazolinyl (such as 3,4-dihydro-4-oxo-quinazolinyl), benzisothiazolyl, benzisoxazolyl, benzodiazinyl, benzofurazanyl, benzothiopyranyl, benzotriazolyl, benzpyrazolyl, dihydrobenzofuryl, dihydrobenzothienyl, dihydrobenzothiopyranyl, dihydrobenzothiopyranyl sulfone, dihydrobenzopyranyl, indolinyl, indazolyl, isochromanyl, isoindolinyl, naphthyridinyl, phthalazinyl, piperonyl, purinyl, pyridopyridyl, quinazolinyl, tetrahydroquinolinyl, thienofuryl, thienopyridyl, thienothienyl, and the like.

Exemplary substituents include one or more alkyl or aralkyl groups as described above or one or more groups described above as alkyl substituents. Also included are smaller heterocycles, such as, epoxides and aziridines.

The term "carbocyclic ring" refers to stable, saturated or partially unsaturated monocyclic hydrocarbon rings of 3 to 7 carbon atoms such as cyclopropyl, cyclobutyl, cyclopentyl, cyclohexyl and cycloheptyl. The term "optionally substituted" as it refers to "carbocyclic ring" herein indicates that the carbocyclic ring may be substituted at one or more substitutable ring positions by one or more groups independently selected from alkyl (preferably lower alkyl), alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy [lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups.

The term "heteroatoms" shall include oxygen, sulfur and nitrogen.

The compounds of formula I may form salts which are also within the scope of this invention. Pharmaceutically acceptable (i.e. non-toxic, physiologically acceptable) salts are preferred, although other salts are also useful, e.g., in isolating or purifying the compounds of this invention.

The compounds of formula I may form salts with alkali metals such as sodium, potassium and lithium, with alkaline earth metals such as calcium and magnesium, with organic bases such as dicyclohexylamine, tributylamine, pyridine and amino acids such as arginine, lysine and the like. Such salts can be formed as known to those skilled in the art.

The compounds for formula I may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid and various others (e.g., nitrates, phosphates, borates, tartrates, citrates, succinates, benzoates, ascorbates, salicylates and the like). Such salts can be formed as known to those skilled in the art.

In addition, zwitterions ("inner salts") may be formed.

All stereoisomers of the compounds of the instant invention are contemplated, either in admixture or in pure or substantially pure form. The definition of compounds according to the invention includes all the possible stereoisomers and their mixtures. Particularly preferred are the racemic forms and the isolated optical isomers having the specified activity. The racemic forms can be resolved by physical methods, such as, for example, fractional crystallization, separation or crystallization of diastereomeric derivatives or separation by chiral column chromatography. The individual optical isomers can be obtained from the racemates from the conventional methods, such as, for example, salt formation with an optically active acid followed by crystallization.

Compounds of the formula I may also have prodrug forms. Any compound that will be converted in vivo to provide the bioactive agent (i.e., the compound for formulas I) is a prodrug within the scope and spirit of the invention.

Various forms of prodrugs are well known in the art. For examples of such prodrug derivatives, see:

a) *Design of Prodrugs*, edited by H. Bundgaard, (Elsevier, 1985) and *Methods in Enzymology*, Vol. 42, p. 309–396, edited by K. Widder, et al. (Academic Press, 1985);

b) *A Textbook of Drug Design and Development*, edited by Krosgaard-Larsen and H. Bundgaard, Chapter 5, "Design and Application of Prodrugs," by H. Bundgaard, p. 113–191 (1991); and c) H. Bundgaard, *Advanced Drug Delivery Reviews,* 8, 1–38 (1992).

It should further be understood that solvates (e.g., hydrates) of the compounds of formula I are also with the scope of the present invention. Methods of solvation are generally known in the art.

Use and Utility

The present invention is based on the discovery that certain pyrrolotriazines are inhibitors of protein kinases. More specifically, pyrrolotriazines such as those described in this invention inhibit the protein tyrosine kinase activity of members of the HER family of receptors. These inhibitors will be useful in the treatment of proliferative diseases that are dependent on signaling by one or more of these receptors. Such diseases include psoriasis, rheumatoid arthritis, and solid tumors of the lung, head and neck, breast, colon, ovary, and prostate. The invention relates to a pharmaceutical composition of compound of formula I, or pharmaceutically acceptable salt or hydrate thereof, and a pharmaceutically acceptable carrier in the treatment of hyperproliferative disorder in mammal. In particular, the said pharmaceutical composition is expected to inhibit the growth of those primary and recurrent solid tumors which are associated with HER1 (EGF receptor) and HER2, especially those tumors which are significantly dependent on HER1 or HER2 for their growth and spread, including for example, cancers of the bladder, squamous cell, head, colorectal, oesophageal, gynecological (such as ovarian), pancreas, breast, prostate, vulva, skin, brain, genitourinary tract, lymphatic system (such as thyroid), stomach, larynx and lung. In another embodiment, the compounds of the present invention are also useful in the treatment of noncancerous disorders such as psoriasis and rheumatoid arthritis.

Thus according to a further aspect of the invention there is provided the use of a compound of the formula I, or a pharmaceutically acceptable salt thereof in the manufacture of a medicament for use in the production of an antiproliferative effect in a mammalian species such as a human being.

According to a further feature of the invention there is provided a method for producing an antiproliferative effect in a mammalian species, such as a human being, in need of such treatment which comprises administering to said animal an effective amount of a compound of formula I or a pharmaceutically acceptable salt thereof as defined herein before.

By virtue of their ability to inhibit HER1, HER2, and HER4 kinases, compounds of the present invention can be used for the treatment of proliferative diseases, including psoriasis and cancer. The HER1 receptor kinase has been shown to be expressed and activated in many solid tumors including head and neck, prostate, non-small cell lung, colorectal, and breast cancer. Similarly, the HER2 receptor kinase has been shown to be overexpressed in breast, ovarian, lung and gastric cancer. Monoclonal antibodies that downregulate the abundance of the HER2 receptor or inhibit signaling by the HER1 receptor have shown anti-tumor efficacy in preclincal and clinical studies. It is therefore expected that inhibitors of the HER1 and HER2 kinases will have efficacy in the treatment of tumors that depend on signaling from either of the two receptors. In addition, these compounds will have efficacy in inhibiting tumors that rely on HER receptor heterodimer signaling. These compounds are expected to have efficacy either as single agent or in combination (simultaneous or sequentially) with other chemotherapeutic agents such as Taxol, adriamycin, and cisplatin. Since HER1 and HER2 signaling has been shown to regulate expression of angiogenic factors such as vascular endothelial growth factor (VEGF) and interleukin 8 (IL8), these compounds are expected to have anti-tumor efficacy resulting from the inhibition of angiogenesis in addition to the inhibition of tumor cell proliferation and survival. The HER2 receptor has been shown to be involved in the hyperproliferation of synovial cells in rheumatoid arthritis, and may contribute to the angiogenic component of that inflammatory disease state. The inhibitors described in this invention are therefore expected to have efficacy in the treatment of rheumatoid arthritis. The ability of these compounds to inhibit HER1 further adds to their use as antiangiogenic agents. See the following documents and references cited therein: Schlessinger J., "Cell signaling by receptor tyrosine kinases", *Cell* 103(2), p. 211–225 (2000); Cobleigh, M. A., Vogel, C. L., Tripathy, D., Robert, N. J., Scholl, S., Fehrenbacher, L., Wolter, J. M., Paton, V., Shak, S., Lieberman, G., and Slamon, D. J., "Multinational study of the efficacy and safety of humanized anti-HER2 monoclonal antibody in women who have HER2-overexpressing metastatic breast cancer that has progressed after chemotherapy for metastatic disease", *J. of Clin. Oncol.* 17(9), p. 2639–2648 (1999); Baselga, J., Pfister, D., Cooper, M. R., Cohen, R., Burtness, B., Bos, M., D'Andrea, G., Seidman, A., Norton, L., Gunnett, K., Falcey, J., Anderson, V., Waksal, H., and Mendelsohn, J., "Phase I studies of anti-epidermal growth factor receptor chimeric antibody C225 alone and in combination with cisplatin", *J. Clin. Oncol.* 18(4), p. 904–914 (2000); Satoh, K., Kikuchi, S., Sekimata, M., Kabuyama, Y., Homma, M. K., and Homma Y., "Involvement of ErbB-2 in rheumatoid synovial cell growth", *Arthritis Rheum.* 44(2), p. 260–265 (2001).

The antiproliferative treatment defined herein before may be applied as a sole therapy or may involve, in addition to a compound of the invention, one or more other substances and/or treatments. Such conjoint treatment may be achieved by way of the simultaneous, sequential or separate administration of the individual components of the treatment. The compounds of this invention may also be useful in combination with known anti-cancer and cytotoxic agents and treatments, including radiation. If formulated as a fixed dose, such combination products employ the compounds of this invention within the dosage range described below and the other pharmaceutically active agent within its approved dosage range. Compounds of formula I may be used sequentially with known anticancer or cytotoxic agents and treatment, including radiation when a combination formulation is inappropriate.

In the field of medical oncology it is normal practice to use a combination of different forms of treatment to treat each patient with cancer. In medical oncology the other component(s) of such conjoint treatment in addition to the antiproliferative treatment defined herein before may be: surgery, radiotherapy or chemotherapy. Such chemotherapy may cover three main categories of therapeutic agent:

(i) antiangiogenic agents that work by different mechanisms from those defined hereinbefore (for example, linomide, inhibitors of integrin αvβ3 function, angiostatin, razoxane);

(ii) cytostatic agents such as antiestrogens (for example, tamoxifen, toremifene, raloxifene, droloxifene, iodoxifene), progestogens (for example megestrol acetate), aromatase inhibitors (for example, anastrozole, letrozole, borazole, exemestane), antihormones, antiprogestogens, antiandrogens (for example, flutamide, nilutamide, bicalutamide, cyproterone acetate), LHRH agonists and antagonists (for example, gosereline acetate, leuprolide), inhibitors of testosterone 5α-dihydroreductase (for example, finasteride), farnesyltransferase inhibitors, anti-invasion agents (for example, metalloproteinase inhibitors like marimastat and inhibitors of urokinase plasminogen activator receptor function) and inhibitors of growth factor function, (such growth factors include for example, EGF, FGF, platelet derived growth factor and hepatocyte growth factor such inhibitors include growth factor antibodies, growth factor receptor antibodies such as Avastin® (bevacizumab) and Erbitux® (cetuximab); tyrosine kinase inhibitors and serine/threonine kinase inhibitors); and (iii) antiproliferative/antineoplastic drugs and combinations thereof, as used in medical oncology, such as antimetabolites (for example, antifolates like methotrexate, fluoropyrimidines like 5-fluorouracil, purine and adenosine analogues, cytosine arabinoside); Intercalating antitumour antibiotics (for example, anthracyclines like doxorubicin, daunomycin, epirubicin and idarubicin, mitomycin-C, dactinomycin, mithramycin); platinum derivatives (for example, cisplatin, carboplatin); alkylating agents (for example, nitrogen mustard, melphalan, chlorambucil, busulphan, cyclophosphamide, ifosfamide nitrosoureas, thiotepa; antimitotic agents (for example, vinca alkaloids like vincristine, vinorelbine, vinblastine and vinflunine, and taxoids like Taxol® (paclitaxel), Taxotere® (docetaxel) and newer microbtubule agents such as epothilone analogs, discodermolide analogs, and eleutherobin analogs); topoisomerase inhibitors (for example, epipodophyllotoxins like etoposide and teniposide, amsacrine, topotecan and irinotecan); cell cycle inhibitors (for example, flavopyridols); biological response modifiers and proteasome inhibitors such as Velcade® (bortezomib).

As stated above, the formula I compounds of the present invention are of interest for their antiproliferative effects. Such compounds of the invention are expected to be useful in a wide range of disease states including cancer, psoriasis, and rheumatoid arthritis.

More specifically, the compounds of formula I are useful in the treatment of a variety of cancers, including (but not limited to) the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, and osteosarcoma.

Due to the key role of kinases in the regulation of cellular proliferation in general, inhibitors could act as reversible cytostatic agents which may be useful in the treatment of any disease process which features abnormal cellular proliferation, e.g., benign prostate hyperplasia, familial adenomatosis polyposis, neuro-fibromatosis, pulmonary fibrosis, arthritis, psoriasis, glomerulonephritis, restenosis following angioplasty or vascular surgery, hypertrophic scar formation and inflammatory bowel disease The compounds of formula I are especially useful in treatment of tumors having a high incidence of tyrosine kinase activity, such as colon, lung, and pancreatic tumors. By the administration of a composition (or a combination) of the compounds of this invention, development of tumors in a mammalian host is reduced.

Compounds of formula I may also be useful in the treatment of diseases other than cancer that may be associated with signal transduction pathways operating through growth factor receptors such as HER1 (EGF receptor), HER2, or HER4.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

The compounds may be administered in a dosage range of about 0.05 to 300 mg/kg/day, preferably less than 200 mg/kg/day, in a single dose or in 2 to 4 divided doses.

Biological Assays

HER1, HER2 or HER4 Kinase Assays

Compounds of interest were assayed in a kinase buffer that contained 20 mM Tris.HCl, pH 7.5, 10 mM $MnCl_2$, 0.5 mM dithiothreitol, bovine serum albumin at 0.1 mg/ml, poly(glu/tyr, 4:1) at 0.1 mg/ml, 1 µM ATP, and 4 µCi/ml [$\gamma$-$^{33}$P]ATP. Poly(glu/tyr, 4:1) is a synthetic polymer that serves as a phosphoryl acceptor and is purchased from Sigma Chemicals. The kinase reaction is initiated by the addition of enzyme and the reaction mixtures were incubated at 26° C. for 1 h. The reaction is terminated by the addition of EDTA to 50 mM and proteins are precipitated by the addition of trichloroacetic acid to 5%. The precipitated proteins are recovered by filtration onto Packard Unifilter plates and the amount of radioactivity incorporated is measured in a Topcount scintillation counter.

For the preparation of recombinant HER1 and HER4, the cytoplasmic sequences of the receptors were expressed in insect cells as GST fusion proteins, which were purified by affinity chromatography. The cytoplasmic sequence of HER2 was subcloned into the baculovirus expression vector pBlueBac4 (Invitrogen) and was expressed as an untagged protein in insect cells. The recombinant protein was partially purified by ion-exchange chromatography.

The instant compounds inhibit HER1, HER2, and HER4 kinases with $IC_{50}$ values between 0.001 and 25 µM. Preferred compounds have $IC_{50}$ values between 0.001–5.0 µM. More preferred compounds have $IC_{50}$ values between 0.001–1.0 µM. Most preferred compounds have $IC_{50}$ values between 0.001–0.1 µM.

Methods of Preparation

Certain compounds of formula I may generally be prepared according to the following schemes and the knowledge of one skilled in the art. Supplemental preparation information may also be found in co-pending U.S. patent application Ser. No. 09/573,829 filed May 18, 2000 and international applications published under the Patent Cooperation Treaty (PCT), International Publication Number WO 00/71129 and WO 03/042172, all of which are incorporated by reference herein.

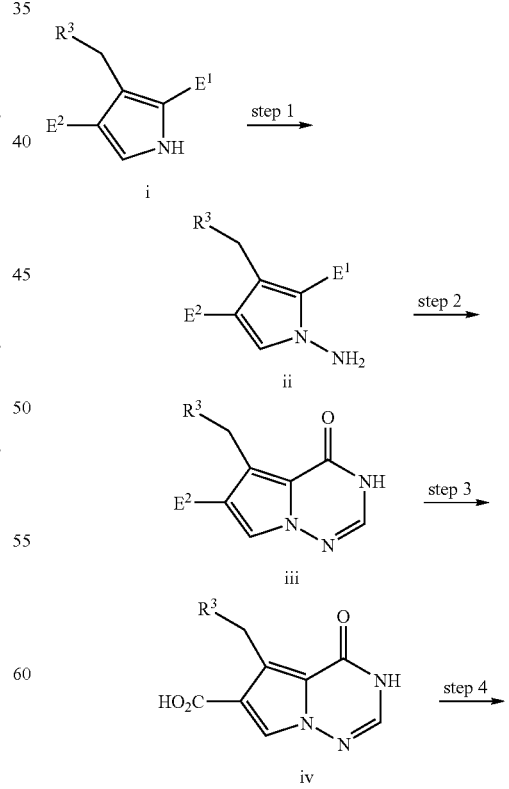

Scheme 1

-continued

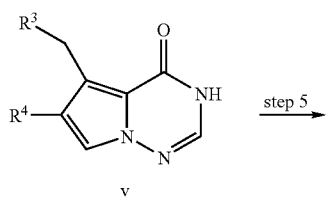

wherein $E^1$, $E^2$ are ester groups and $A^1$ is a halogen

Step 1
The first step of Scheme 1 is accomplished by treatment of a 3-alkyl-1H-pyrrole-2,4-dicarboxylic acid ester i (T. D. Lash et al., J. Heterocyclic Chem., 1991, 28, 1671) with a base such as potassium t-butoxide or sodium hydride in an anhydrous solvent such as THF or DMF followed by an aminating reagent, such as O-(2,4-dinitro-phenyl)-hydroxylamine (T. Sheradsky, J. Heterocyclic Chem., 1967, 4, 413) or chloramine (I. P. Sword, J. Chem. Soc. C, 1971, 820) to give the pyrrolylamine ii.

Step 2
The pyrrolylamine ii is heated with excess formamide to give the pyrrolotriazinone iii.

Step 3
The ester iii can be saponified by treatment with a base as an aqueous solution of lithium hydroxide and then acidified by treatment with an acid such as HCl to give the carboxylic acid iv.

Step 4
The carboxylic acid iv is converted to the intermediate v under appropriate conditions. For example, the acid iv is decarboxylated by heating a mixture of iv in 85% phosphoric acid at 110° C. to give 6H-pyrrolotrazin-4-one v ($R^4$=H)

Step 5
Compound v is converted to a 4-halopyrrolotriazine vi, e.g., the 4-chloro-pyrrolotriazine, by heating v with phosphorus oxychloride.

Scheme 2

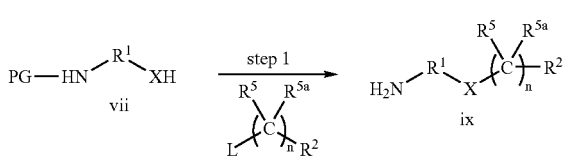

PG is a protecting group and L is a leaving group
An appropriately protected compound vii can be treated with an alkylating agent viii to provide compound ix after a suitable deprotection. This can be accomplished under a variety of conditions, for example, a nitrophenol vii is treated with an alcohol viii and a base such as potassium carbonate in an appropriate solvent such as DMA. The resulting intermediate is reduced under appropriate conditions, such as heating with iron powder in acetic acid, to give the corresponding compound ix.

Scheme 3

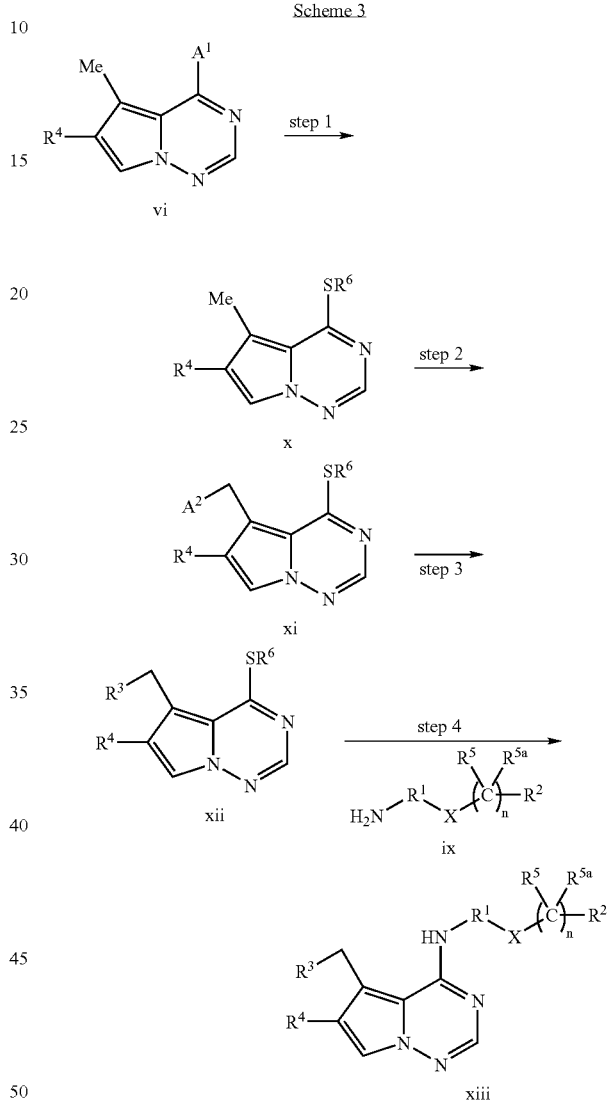

wherein $A^1$ = halogen; $A^2$ = halogen; $R^6$ = alkyl

Step 1
The 4-halo-pyrrolotriazine vi ($R^3$=H) is converted to the corresponding 4-thioalkyl derivative x by treatment with an appropriate reagent such as NaSMe.

Step 2
Halogenation of the 5-methyl group of Compound x can be effected by treatment with a halogenating agent such as NBS or sulfuryl chloride. The reaction is performed under an inert atmosphere in the presence of a catalyst such as dibenzoyl peroxide or 2,2'-azobisisobutyronitrile, or irradiation and gives the 5-halomethyl-pyrrolotriazine xi.

Step 3

Treatment of xi with an appropriate nucleophile such as a thiol, thiocarboxylic acid, water, an alcohol, a carboxylic acid, a primary or secondary amine in the presence of a base such as sodium bicarbonate or triethylamine in a solvent such as acetonitirile affords intermediate xii.

Step 4

A mixture of compound xii and compound ix is heated in the presence of a reagent such as $HgCl_2$ in a solvent such as toluene. Subsequent aqueous workup provides the final product xiii.

Step 3

A mixture of compound xv and ix can be heated in a solvent such as DMA to produce the coupled product xvi.

Step 4

Treatment of xvi with an appropriate nucleophile such as thiol, thiocarboxylic acid, water, an alcohol, a carboxylic acid or a primary or secondary amine in the presence of a base such as diisopropylethylamine in a solvent such as DMF affords the final product xiii.

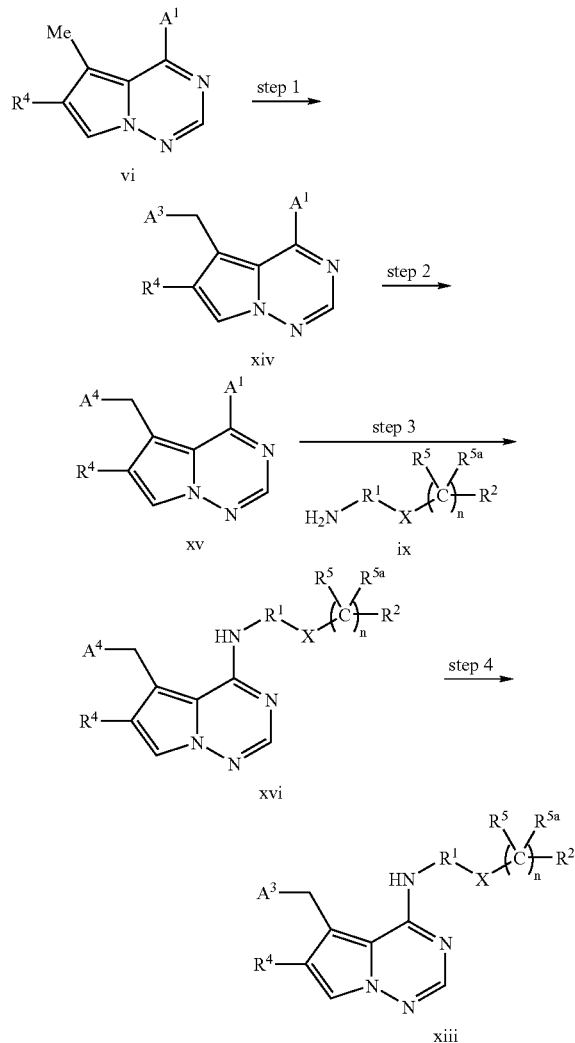

Scheme 4

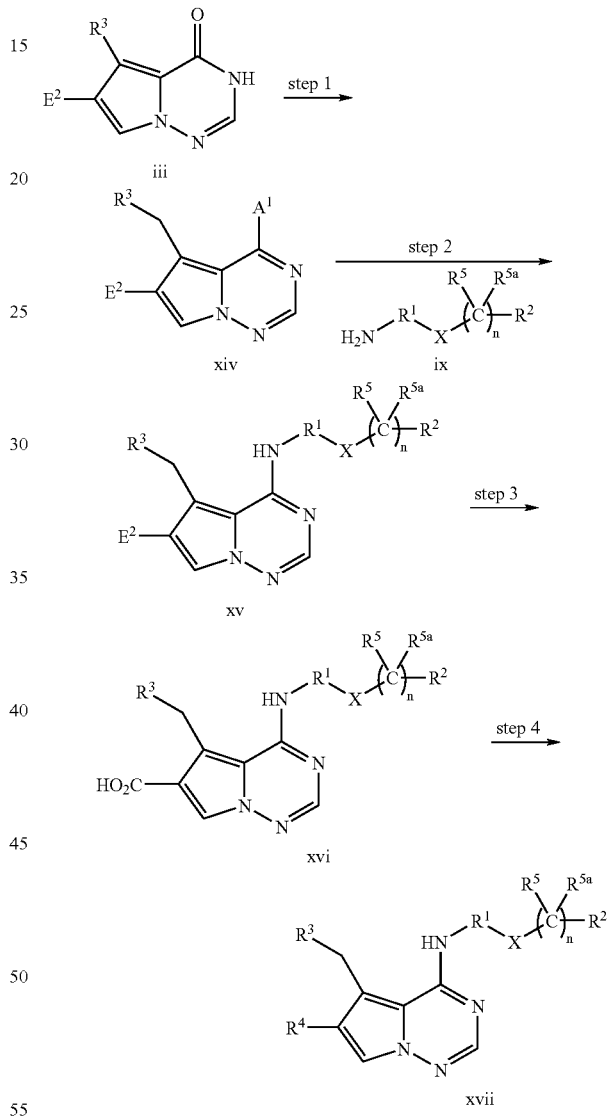

Scheme 5

$A^1$ and $A^3$ are halogen and $A^4$ is a leaving group

Step 1

Halogenation of the 5-methyl group of compound vi can be effected as described in Scheme 3 to give the halomethyl pyrrolotriazine xiv.

Step 2

The halogen $A^3$ of compound xiv can be converted into an appropriate leaving group $A^4$, such as a triethylammonium bromide salt, which is obtained by treatment with triethylamine and THF at ambient temperature. This affords compound xv.

Step 1

Compound iii is converted to a 4-halo-pyrrolotriazine xiv by heating with the corresponding phosphorus oxyhalide, e.g., the 4-chloro-pyrrolotriazine is obtained by heating iii with phosphorus oxychloride.

Step 2

Treatment of the amine ix with the 4-halo-pyrrolotriazine xiv in the presence of a base such as diisopropylethylamine in a solvent such as acetonitrile gives the coupled product xv.

Step 3

The carboxylic acid ester xv can be saponified by treatment with a base such as an aqueous solution of sodium hydroxide and then acidified by treatment with an acid such as HCl to give the carboxylic acid xvi.

Step 4

Conversion of the carboxylic acid xvi to the final product xvii can be accomplished under a variety of conditions. For example, the carboxylic acid can be converted to the corresponding isocyanate via Curtius rearrangement by treatment with an appropriate azide such as diphenylphosphorazidate in the presence of a base such as triethylamine. The intermediate isocyanate can be trapped with an appropriate nucleophile such as an alcohol or an amine to give the corresponding urea or urethane xvii.

In addition, other compounds of formula I may be prepared using procedures generally known to those skilled in the art. In particular, the following examples provide additional methods for the preparation of the compounds of this invention.

EXAMPLE 1

[5-(4-Amino-piperidin-1-ylmethyl)-pyrrolo[2,1-f][1,2,4]triazin-4-yl]-[3-chloro-4-(pyridin-2-ylmethoxy)-phenyl]-amine

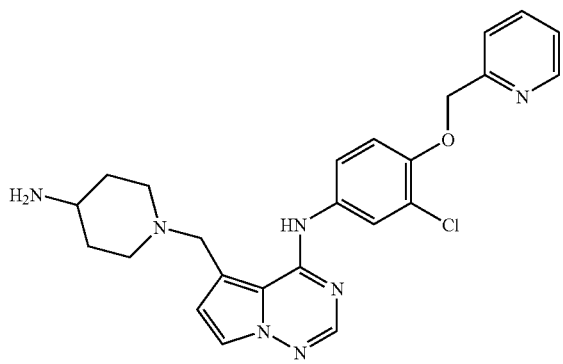

1A. Preparation of 5-methyl-4-methylsulfanyl-pyrrolo[2,1f][1,2,4]triazine

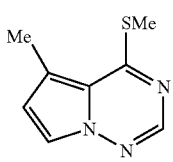

To a solution of 4-chloro-5-methyl-pyrrolo[2,1f][1,2,4]triazine (4.02 g, 24.0 mmol) (Ref. WO 03/042172 A2) in dry THF (200 ml) sparged with $N_2$ at 0° C. was added NaSMe (1.85 g, 26.3 mmol). The sparging was continued for 5 min. The reaction mixture was then stirred at rt overnight and concentrated in vacuo to about 50 ml volume left. The mixture was diluted with $H_2O$ (280 ml) and stirred at 0° C. The solid was filtered, washed with cold water and dried to give 1A (3.91 g, 91%). Analytical HPLC retention time=3.38 min. (YMC S5 ODS column 4.6×50 mm, 10–90% aqueous methanol over 4 minutes containing 0.2% phosphoric acid, 4 mL/min, monitoring at 220 nm) and a LC/MS $M^+ +1=180$.

1B. Preparation of [1-(4-methylsulfanyl-pyrrolo[2,1-f][1,2,4]triazin-5-ylmethyl)-piperidin-4-yl]-carbamic acid tert-butyl ester

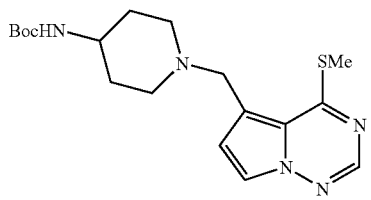

A mixture of 1A (1.94 g, 10.8 mmol), benzoyl peroxide (0.262 g, 1.08 mmol), NBS (2.12 g, 11.90 mmol) in $CCl_4$ (100 ml) was sparged with $N_2$, then immediately heated to 85° C. for 1.5 h. The mixture was cooled to rt and the precipitate was filtered off. The filtrate was concentrated in vacuo, and diluted with dichloroethane (35 ml). DIEA (2.24 ml, 12.96 mmol) and piperidin-4-yl-carbamic acid tert-butyl ester (2.38 g, 11.90 mmol) were added. The reaction mixture was stirred at rt for 1 h. The mixture was diluted with saturated $NaHCO_3$ (70 ml) and extracted with EtOAc (3×100 ml). The combined EtOAc extracts were washed with brine (1×100 ml), dried ($MgSO_4$), filtered and concentrated in vacuo. The residue was purified by silica gel flash column to give 1B (2.87 g, 70%)(0.1%–2% MeOH—$CH_2Cl_2$). Analytical HPLC retention time=2.12 min. (YMC S5 ODS column 4.6×50 mm, 10–90% aqueous methanol over 4 minutes containing 0.2% phosphoric acid, 4 mL/min, monitoring at 220 nm) and a LC/MS $M^+ +1=378$.

1C. Preparation of 3-chloro-4-(pyridin-2-ylmethoxy)-phenylamine

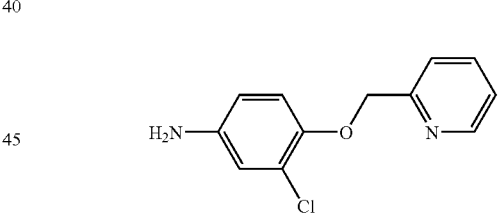

To a mixture of 4-amino-2-chloro-phenol (1.0 g, 6.96 mmol), 2-hydroxymethylpyridine (1.52 g, 13.92 mmol), $Ph_3P$ (3.65 g, 13.92 mmol) in THF (30 ml) was added DIAD (2.74 ml, 13.92 mmol). The reaction mixture was stirred overnight and then concentrated in vacuo, and dissolved in EtOAc (100 ml). The resulting solution was extracted with 1N HCl (60 ml); the aqueous layer was washed with EtOAc (2×60 ml), then basified with solid $NaHCO_3$. The mixture was extracted with EtOAc (2×100 ml) and the combined EtOAc extracts were washed with brine (1×40 ml), dried ($MgSO_4$), filtered and concentrated in vacuo. The residue was purified by silica gel flash column to give 1C (0.54 g, 33%) (50%–80% EtOAc-Hexanes). Analytical HPLC retention time=0.61 min. (YMC S5 ODS column 4.6×50 mm, 10–90% aqueous methanol over 4 minutes containing 0.2% phosphoric acid, 4 mL/min, monitoring at 220 nm) and a LC/MS $M^+ +1=235$.

1D. Preparation of 5-bromomethyl-4-chloro-pyrrolo[2,1f][1,2,4]triazine (Ref. WO 03/042172 A2)

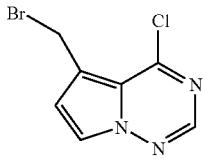

A solution of 4-chloro-5-methyl-pyrrolo[2,1f][1,2,4]triazine (17.24 g, 102.9 mmol) (Ref. WO 03/042172 A2) and AIBN (1.70 g, 10.4 mmol) in CCl$_4$ (500 ml) was sparged with N$_2$ for 2 min. The mixture was heated to reflux in a 100° C. oil bath under N$_2$. NBS (21.94 g, 123.3 mmol) was added portionwise quickly and the resulting mixture was refluxed under N$_2$ for 25 min. The mixture was cooled to rt and the solid was rinsed with CCl$_4$ (2×25 ml). The filtrate was washed with cold dilute NaHCO$_3$ solution (2×200 ml), dried (MgSO$_4$), filtered and concentrated in vacuo to give 1D (24.8 g, 98%).

1E. Preparation of (4-chloro-pyrrolo[2,1-f][1,2,4]triazin-5-ylmethyl)-triethyl-ammonium bromide

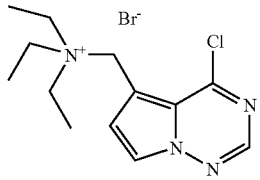

A mixture of 1D (2.7 g, 11 mmol) (Ref. WO 03/042172 A2), Et$_3$N (5 ml, 36 mmol) in THF (20 ml) was stirred at rt over weekend. The solid was filtered and rinsed with THF and Et$_2$O and dried to give 1E (3.38 g, 89%).

1F. Preparation of (1-{4-[3-chloro-4-(pyridin-2-yl-methoxy)-phenylamino]-pyrrolo[2,1-f][1,2,4]triazin-5-ylmethyl}-piperidin-4-yl)-carbamic acid tert-butyl ester

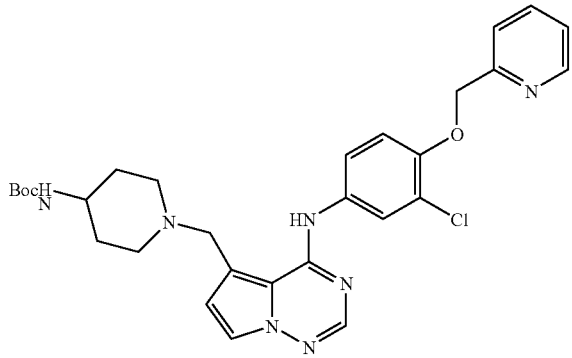

Method One:

A mixture of 1B (77.6 mg, 0.21 mmol), 1C (48 mg, 0.21 mmol) and HgCl$_2$ (66 mg, 0.24 mmol) in toluene (1.2 ml) was heated at 120° C. for 6 h. The mixture was cooled to rt and diluted with saturated NaHCO$_3$ (30 ml). The mixture was extracted with EtOAc (2×50 ml), and the combined EtOAc extracts was washed with brine (1×20 ml), dried (MgSO$_4$), filtered and concentrated in vacuo to give 1F (65 mg, 56%). ). Analytical HPLC retention time=2.67 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=564.

Method Two:

A mixture of 1E (3.00 g, 8.63 mmol) and 1C (2.056 g, 8.63 mmol) in DMA (18 ml) was heated at 70° C. for 3 h and cooled to rt. The cooled mixture was added dropwise to a stirred solution of piperidin-4-yl-carbamic acid tert-butyl ester (1.81 g, 11.90 mmol) and DIEA (3.0 ml, 17.26 mmol) in DMA (12 ml) at 70° C. under N$_2$ over 40 min. The resulting mixture was stirred for 2 h, cooled to rt, diluted with H$_2$O (100 ml) and extracted with EtOAc (2×120 ml). The combined EtOAc extracts were washed with saturated NaHCO$_3$ (3×100 ml), brine (1×100 ml), dried (MgSO$_4$), filtered and concentrated. The residue was purified by flash silica gel column to give 1F(3.1 g, 64%) (40%–50% EtOAc-hexanes). Analytical HPLC retention time=2.67 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=564.

1G. Preparation of [5-(4-amino-piperidin-1-ylmethyl)-pyrrolo[2,1-f][1,2,4]triazin-4-yl]-[3-chloro-4-(pyridin-2-yl-methoxy)-phenyl]-amine

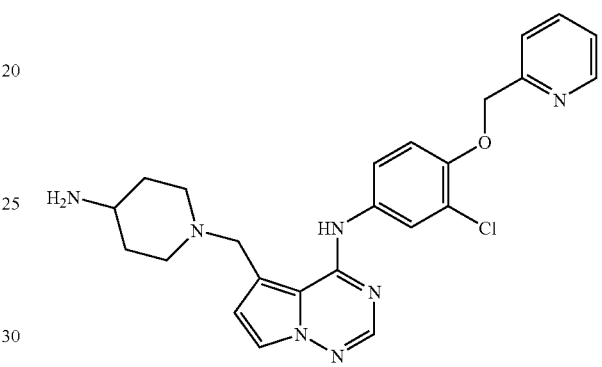

To a solution of 1F (65 mg, 0.12 mmol) in CH$_2$Cl$_2$ (2 ml) was added TFA (2 ml). The mixture was stirred for 25 min, then concentrated in vacuo. The residue was purified by a Shimadzu auto prep HPLC, employing 30% to 100% 10 min gradient elution with 0.1%TFA in MeOH-water solvent system, 220 nM detection, 20 mL/min elution with a YMC ODS S5 20×100 mm column to give the desired 1G (33 mg, 62%). Analytical HPLC retention time=1.48 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=464.

EXAMPLE 2

[5-(4-Amino-piperidin-1-ylmethyl)-pyrrolo[2,1-f][1,2,4]triazin-4-yl]-[3-chloro-4-(pyridin-3-ylmethoxy)-phenyl]-amine

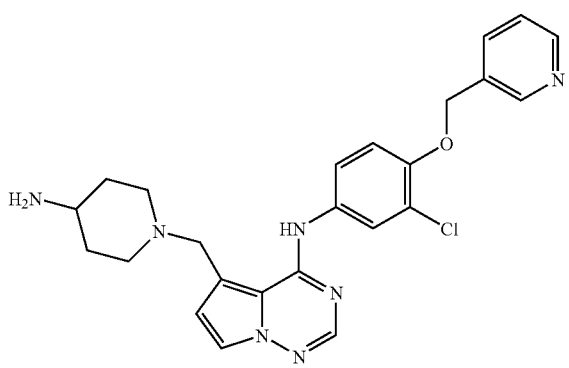

2A. Preparation of 3-chloro-4-(pyridin-3-ylmethoxy)-phenylamine

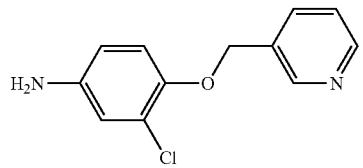

Compound 2A (0.84 g, 51%) was prepared from 4-amino-2-chloro-phenol (1.0 g, 6.96 mmol), 3-hydroxymethylpyridine (1.52 g, 13.9 mmol) by a route analogous to that used for the preparation of 1C.

2B. Preparation of (1-{4-[3-chloro-4-(pyridin-3-ylmethoxy)-phenylamino]-pyrrolo[2,1-f][1,2,4]triazin-5-ylmethyl}-piperidin-4-yl)-carbamic acid tert-butyl ester

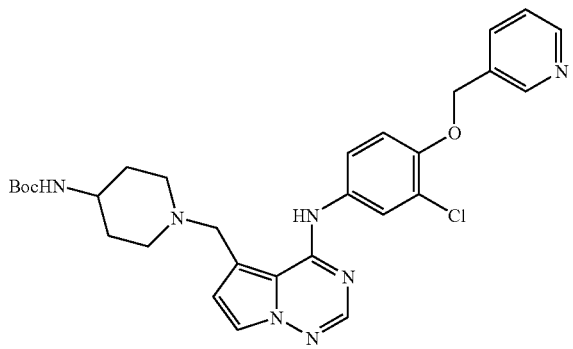

Compound 2B (78 mg, 61%) was prepared from 1B (86 mg, 0.23 mmol) and 2A (86 mg, 0.37 mmol) by a route analogous to that used for the preparation of 1F (method one).

2C. Preparation of [5-(4-amino-piperidin-1-ylmethyl)-pyrrolo[2,1-f][1,2,4]triazin-4-yl]-[3-chloro-4-(pyridin-3-ylmethoxy)-phenyl]-amine

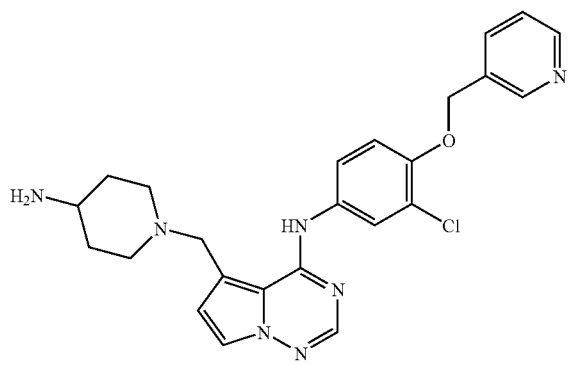

Compound 2C (34 mg, 51%) was prepared from 2B (78 mg, 0.14 mmol) by a route analogous to that used for the preparation of 1G. Compound 2C had an analytical HPLC retention time=1.13 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=464.

EXAMPLE 3

(S)-[3-Chloro-4-(3-fluoro-benzyloxy)-phenyl]-[5-(morpholin-2-ylmethoxymethyl)-pyrrolo[2,1-f][1,2,4]triazin-4-yl]-amine

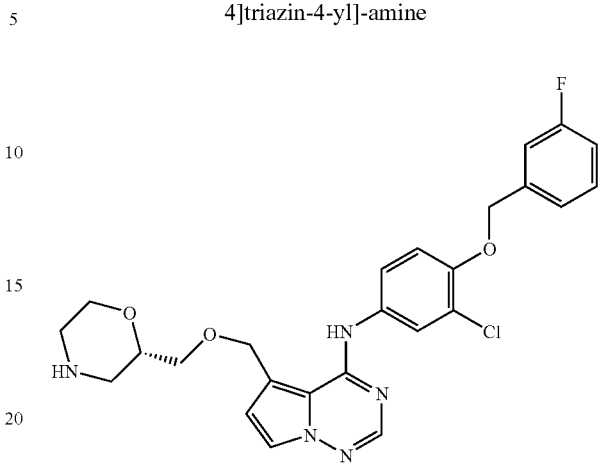

3A. Preparation of 3-chloro-4-(3-fluoro-benzyloxy)-phenylamine

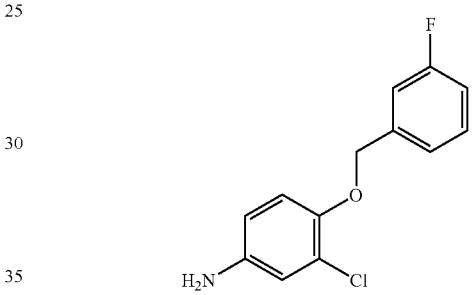

Compound 3A (1.65 g, 78%) was prepared from 4-amino-2-chloro-phenol (1.06 g, 7.38 mmol), 3-fluorobenzyl alcohol (2.4 g, 16.8 mmol) by a route analogous to that used for the preparation of 1C.

3B. Preparation of {4-[3-chloro-4-(3-fluoro-benzyloxy)-phenylamino]-pyrrolo[2,1-f][1,2,4]triazin-5-yl}-methanol

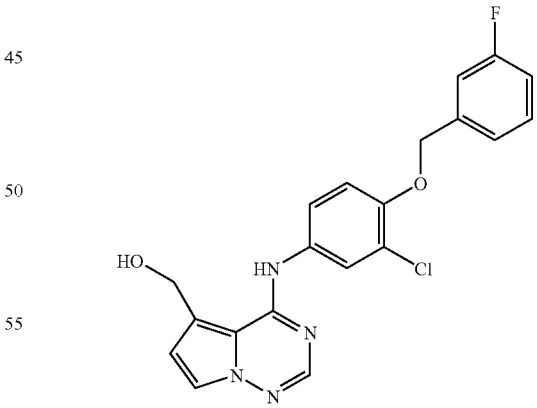

A mixture of 1D (228 mg, 0.92 mmol), NaHCO$_3$ (156 mg, 1.85 mmol) in CH$_3$CN (3.1 ml) and H$_2$O (0.3 ml) was stirred at rt for 2 days. Some anhydrous Na$_2$SO$_4$ was added, followed by aniline 3A (233 mg, 1.85 mmol). The reaction mixture was stirred overnight. The precipitate was filtered off and the solid was rinsed with CH$_2$Cl$_2$ (6×10 ml). The filtrate was concentrated in vacuo, and the residue was purified by a Shimadzu auto prep HPLC, employing 30% to 100% 10 min gradient, 6 min 100% holding, elution with 0.1%TFA in MeOH-water solvent system, 220 nM detection, 20 mL/min elution with a YMC ODS S5 20×100 mm column to give the desired 3B (34 mg, 9.2%). Analytical HPLC retention time=3.74 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=399.

3C. Preparation of (S)-2-{4-[3-chloro-4-(3-fluoro-benzyloxy)-phenylamino]-pyrrolo[2,1-f][1,2,4]triazin-5-yl-methoxy methyl}-morpholine-4-carboxylic acid tert-butyl ester

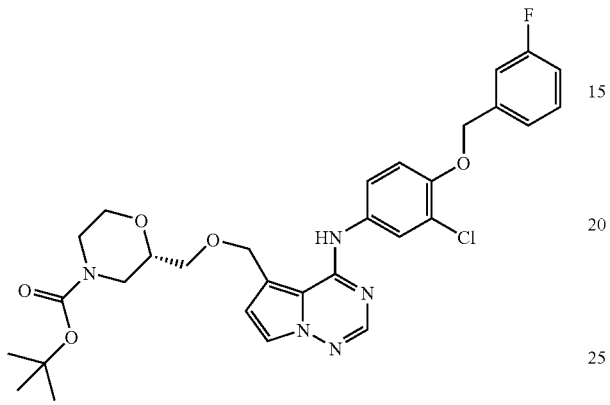

To a suspension of 3B (33.6 mg, 0.084 mmol) in CH$_2$Cl$_2$ (1.6 ml) was added SOCl$_2$ (6.8 μl, 0.093 mmol). The mixture was stirred for 15 min, then (S)-2-hydroxymethyl-morpholine-4-carboxylic acid tert-butyl ester (27.4 mg, 0.126 mmol) was added, followed by DIEA (16.1 μl, 0.093 mmol). The resulting mixture was stirred at rt rigorously overnight, then heated between 45–65° C. for 2 h. Cooled to rt, concentrated in vacuo. The residue was purified by a Shimadzu auto prep HPLC, employing 30% to 100% 10 min gradient, 10 min 100% holding, elution with 0.1%TFA in MeOH-water solvent system, 220 nM detection, 20 mL/min elution with a YMC ODS S5 20×100 mm column to give the desired 3C (27.9 mg, 55%). It had an analytical HPLC retention time=4.58 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=598.

3D. Preparation of (S)-[3-chloro-4-(3-fluoro-benzyloxy)-phenyl]-[5-(morpholin-2-ylmethoxymethyl)-pyrrolo[2,1-f][1,2,4]triazin-4-yl]-amine

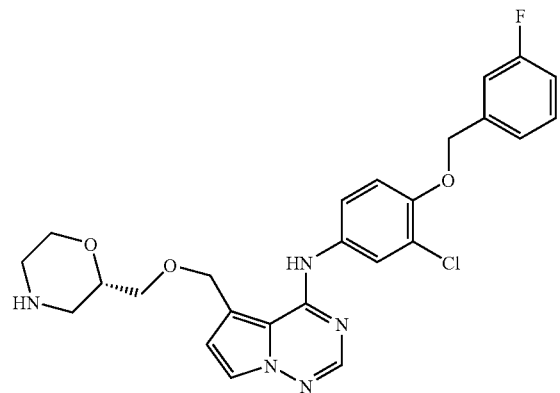

Compound 3D (9.0 mg, 33%) was prepared from 3C (23 mg, 0.038 mmol) by a route analogous to that used for the preparation of 1G. Compound 3D had an analytical HPLC retention time=3.26 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=498.

EXAMPLE 4

(R)-{4-[3-Chloro-4-(3-fluoro-benzyloxy)-phenylamino]-5-methyl-pyrrolo[2,1-f][1,2,4]triazin-6-yl}-carbamic acid morpholin-3-ylmethyl ester

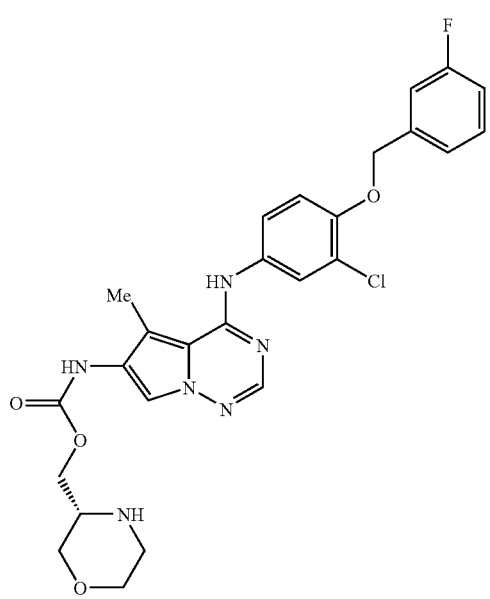

4A. Preparation of 4-Chloro-5-methyl-pyrrolo[2,1-f][1,2,4]triazine-6-carboxylic acid ethyl ester

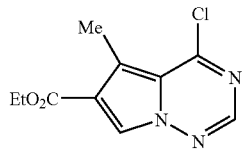

A 2L 3-neck flask was charged with 5-methyl-4-oxo-3,4-dihydro-pyrrolo[2,1-f][1,2,4]triazine-6-carboxylic acid ethyl ester (50 g, 226 mmol) and dry toluene (750 ml). POCl$_3$ (41.6 g, 271.5 mmol) was added in one portion, followed by slow addition of DIEA (32.2 g, 248.9 mmol) at a rate, which maintained the temperature below 30° C. The resulting suspension was heated to 111° C. for 24 h becoming homogeneous at 80° C. The reaction was monitored by HPLC after quenching with 2 M MeNH$_2$/THF (10 μl reaction mixture, 20 μl MeNH$_2$/THF in 200 μl acetonitrile). Upon completion, reaction was cooled to −8° C. and a solution of K$_2$HPO$_4$ in H$_2$O (170 g/775 ml) was added maintaining temperature below 1° C. The mixture was stirred for 20 min at −8° C. then warmed to ambient temperature for 1 h. The resulting light suspension was filtered through a pad of celite and the layers were separated. The organic layer was washed with K$_2$HPO$_4$ in H$_2$O (27 g/130 ml), followed by water (250 ml) and dried (Na$_2$SO$_4$). The solution was filtered and concentrated to a yellow foam 4A (54.0 g, 100%). MS: 235 (MeNH$_2$ adduct) (M+H)$^+$; HPLC Ret Time (MeNH$_2$ adduct): 2.240 min (YMC S5 ODS 4.6×50 mm column, 4 min gradient, 3 mL/min).

4B. Preparation of 4-[3-chloro-4-(3-fluoro-benzyloxy)-phenylamino]-5-25 methyl-pyrrolo[2,1-f][1,2,4]triazine-6-carboxylic acid ethyl ester

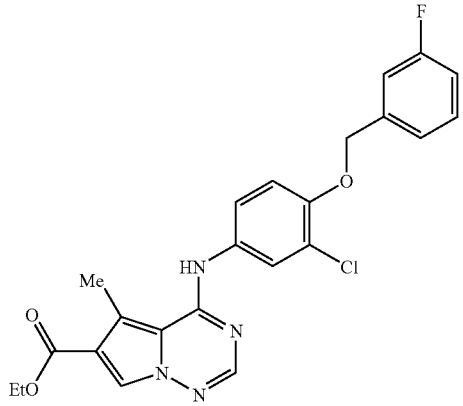

A mixture of 4A (308 mg, 1.29 mmol), 3A (356 mg, 1.41 mmol) and DIEA (0.25 ml, 1.41 mmol) in CH$_3$CN (3.6 ml) was heated at 60° C. overnight. The mixture was cooled to rt and the precipitate was collected, rinsed with CH$_3$CN (3×10 ml), dried by air to give 4B (327 mg, 56%) as white solid. Analytical HPLC retention time=4.14 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=455.

4C. Preparation of 4-[3-chloro-4-(3-fluoro-benzyloxy)-phenylamino]-5-methyl-pyrrolo[2,1-f][1,2,4]triazine-6-carboxylic acid

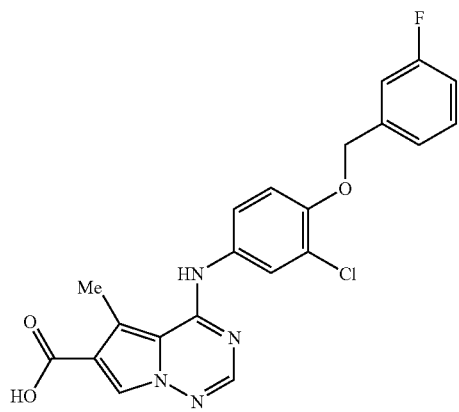

To a suspension of 4B (308 mg, 0.68 mmol) in a mixed solvent of THF (1.5 ml) and MeOH (0.8 ml) was added 50% NaOH (0.23 ml). The mixture was stirred at 65° C. for 3 h. The mixture was cooled to rt and acidified to pH 2 by concentrated HCl. The precipitate was collected, rinsed with H$_2$O (4×5 ml) and dried under vacuum to give 4C (251 mg, 87%) as a white solid. Analytical HPLC retention time=3.76 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=427.

4D. Preparation of (R)-3-{4-[3-chloro-4-(3-fluoro-benzyloxy)-phenylamino]-5-methyl-pyrrolo[2,1-f][1,2,4]triazin-6-ylcarbamoyloxymethyl}-morpholine-4-carboxylic acid tert-butyl ester

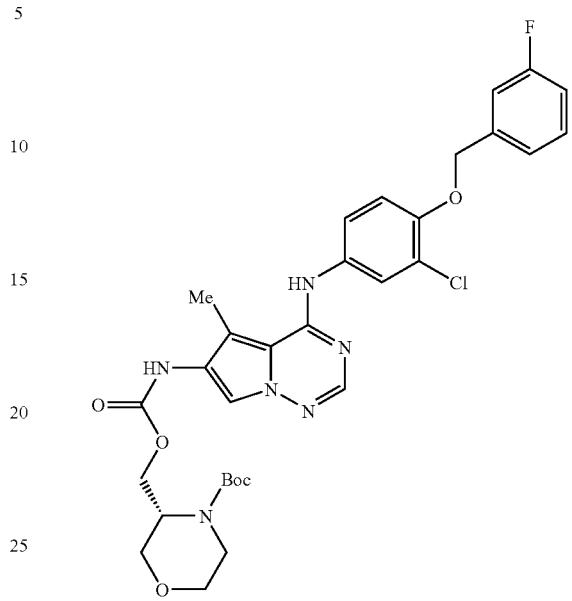

A mixture of 4C (150 mg, 0.35 mmol), DPPA (0.11 ml, 0.53 mmol) and Et$_3$N (0.12 ml, 0.88 mmol) in toluene (3.5 ml) was heated at 55° C. for 3 h. Additional DPPA (0.02 ml, 0.10 mmol) was added, and the mixture was stirred at this temperature for another 1 h. (S)-3-Hydroxymethyl-morpholine-4-carboxylic acid tert-butyl ester (115 mg, 0.53 mmol) was added, and the resulting mixture was heated at 80° C. overnight. The mixture was cooled to rt, diluted with EtOAc (80 ml), washed with H$_2$O (1×30 ml), saturated Na$_2$CO$_3$ (2×30 ml) and brine (1×30 ml). The mixture was dried (MgSO$_4$), filtered and concentrated. The residue was triturated in MTBE (20 ml) and filtered to give 4D (124 mg, 55%) which was used in the next step without further purification.

4E. Preparation of (R)-{4-[3-chloro-4-(3-fluoro-benzyloxy)-phenylamino]-5-methyl-pyrrolo[2,1-f][1,2,4]triazin-6-yl}-carbamic acid morpholin-3-ylmethyl ester

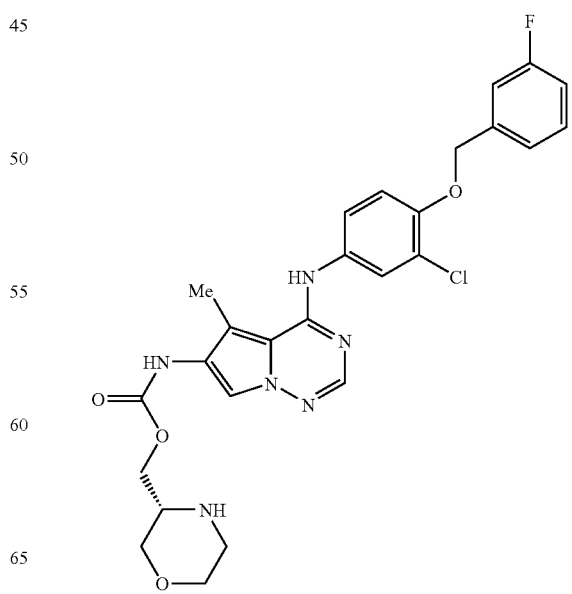

A solution of 4D (100 mg, 0.156 mmol) in TFA (1.2 ml) was stirred at rt for 5 min. The solution was concentrated in vacuo and the residue was purified by a Shimadzu auto prep HPLC, employing 30% to 100% 10 min gradient, 6 min 100% holding elution with 0.1%TFA in MeOH-water solvent system, 220 nM detection, 20 mL/min elution with a YMC ODS S5 20×100 mm column to give 4E (45 mg, 53%). Analytical HPLC retention time=2.93 min. (YMC S5 ODS column 4.6×50 mm, 10–90% aqueous methanol over 4 minutes containing 0.2% phosphoric acid, 4 mL/min, monitoring at 220 nm) and a LC/MS $M^++1=541$.

EXAMPLE 5

[3-Chloro-4-(3-fluoro-benzyloxy)-phenyl]-[5-(piperidin-4-yloxymethyl)-pyrrolo[2,1-f][1,2,4]triazin-4-yl]-amine

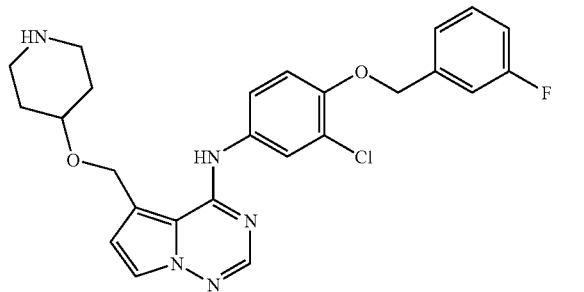

A solution of 5-bromomethyl-4-chloro-pyrrolo[2,1-f][1,2,4]triazine (100 mg, 0.408 mmole), 4-hydroxy-piperidine-1-carboxylic acid tert-butyl ester (1.56 gm, 7.76 mmole) and $NaHCO_3$ (131 mg, 1.56 mmol) in dry acetonitrile (5 mL) was stirred at RT for 3 days. 3-chloro-4-(3-fluoro-benzyloxy)-phenylamine 3A (92 mg, 0.367 mmole) and additional $NaHCO_3$ (131 mg, 1.56 mmol) were added and the reaction was left stirring overnight. The solvent was removed and the residue was partitioned between DCM and water. The organic phase was separated, dried ($Na_2SO_4$), and the solvent removed. The residue was treated with a mixture of TFA:DCM (1:1) at 0° C. for 80 min and the solvents were removed. The residue was taken up in DCM, washed with a sat. aq. $NaHCO_3$ solution and then dried ($Na_2SO_4$). Removal of the solvent followed by radial chromatography (2 mm silica gel plate eluted with DCM containing 5% of a 2 M solution of $NH_3$ in MeOH) afforded the titled product as an oil (85 mg, 43%). Analytical HPLC retention time=1.60 min. (YMC Xterra S7 C18, 3.0×50 mm column, 10–90% aqueous methanol over 2 minutes containing 0.1% TFA, 5 mL/min, monitoring at 220 nm) and a LC/MS $M^++1=482$.

EXAMPLE 6

[4-(3-Fluoro-benzyloxy)-phenyl]-(5-methyl-pyrrolo[2,1-f][1,2,4]triazin-4-yl)-amine

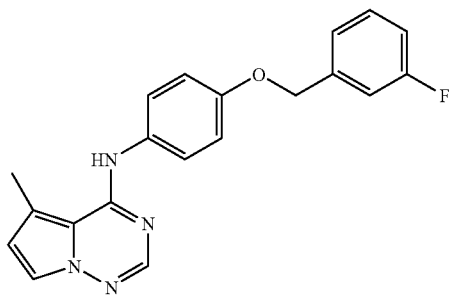

A solution of 4-chloro-5-methyl-pyrrolo[2,1-f][1,2,4]triazine (47 mg, 0.281 mmol) (Ref. WO 03/042172 A2) and 4-(3-fluoro-benzyloxy)-phenylamine hydrochloride (70 mg, 0.299 mmol) and $NaHCO_3$ (600 mg, 7.14 mmol) in dry acetonitrile (2 ml) was heated at 80° C. for 8 hr. Filtration followed by removal of the solvent from the filtrate and purification by preparative HPLC afforded the title product (35 mg, 37%) as an oil. Analytical HPLC retention time=1.41 min. (YMC Xterra S7 C18, 3.0×50 mm column, 10–90% aqueous methanol over 2 minutes containing 0.1% TFA, 5 mL/min, monitoring at 220 nm) and a LC/MS $M^++1=331$.

EXAMPLE 7

[5-(4-Amino-piperidin-1-ylmethyl)-pyrrolo[2,1-f][1,2,4]triazin-4-yl]-[3-chloro-4-(3-fluoro-benzyloxy)-phenyl]-amine

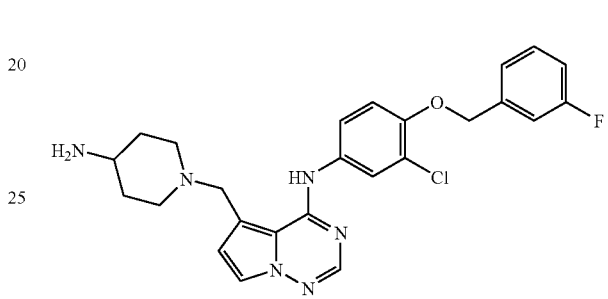

7A. Preparation of [3-chloro-4-(3-fluoro-benzyloxy)-phenyl]-(5-phenylsulfanylmethyl-pyrrolo[2,1-f][1,2,4]triazin-4-yl)-amine

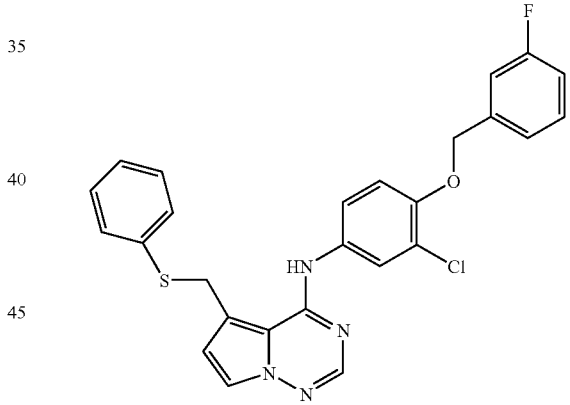

A solution of 5-bromomethyl-4-chloro-pyrrolo[2,1-f][1,2,4]triazine 1D (1.0 g, 4.1 mmol) in DCM (60 ml) was sparged with $N_2$ for 0.5 hr and then placed in a −20° C. bath. Thiophenol (0.42 ml, 4.1 mmol) and diisopropylethylamine (0.713 ml, 4.1 mmol) were added and the reaction was kept at −20° C. for 3 hr. After warming to rt, the reaction mixture was washed with water, dried ($Na_2SO_4$), and the solvent was removed. 1,2-Dichloroethane (20 ml), n-butanol (20 ml) and 3-chloro-4-(3-fluoro-benzyloxy)-phenylamine 3A (900 mg, 3.6 mmol) were added to the residue and the mixture was heated at 85° C. for 2.5 hr. The solvents were removed and the residue was taken up in DCM, washed with sat. aq. $NaHCO_3$ solution and dried ($Na_2SO_4$). Removal of the solvent followed by chromatography on silica gel using DCM containing 0 to 5% MeOH as eluent afforded 7A (0.90 g, 50%) as a foam. LC/MS $M^++1=491$; $^1$H-NMR ($CDCl_3$):δ 4.51 (s, 2H), 5.15 (s, 2H), 6.52 (d, 1H, J=3 Hz), 6.93 (d, 1H, J=9 Hz), 7.02–7.49 (m, 11H), 7.80 (m, 1H, J=3 Hz), 8.18 (s, 1H), 8.74 (s, 1H).

7B. Preparation of (5-benzenesulfinylmethyl-pyrrolo[2,1-f][1,2,4]triazin-4-yl)-[3-chloro-4-(3-fluoro-benzyloxy)-phenyl]-amine

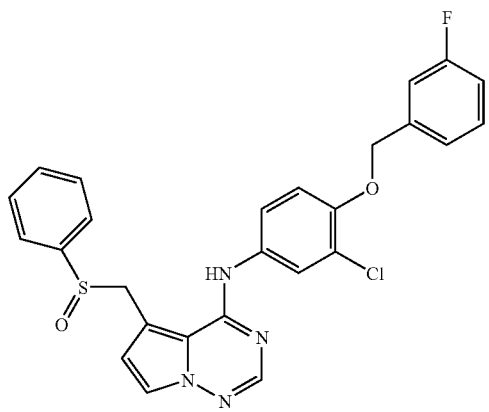

The sulfide 7A (900 mg, 1.63 mmol) was dissolved in chloroform (25 ml), cooled in an ice bath and m-chloroperbenzoic acid (300 mg, 57 to 80%, about 1 equiv) was added in small portions over 15 min. After 1 hr., the reaction was washed with 10% aqueous NaHSO₃ solution, sat. aq. NaHCO₃ solution (three times) and dried (Na₂SO₄). Removal of the solvent afforded 7B (740 mg, 90%) as a foam. Analytical HPLC retention time=1.99 min. (YMC Xterra S7 C18, 3.0×50 mm column, 10–90% aqueous methanol over 2 minutes containing 0.1% TFA, 5 mL/min, monitoring at 220 nm) and a LC/MS M$^+$+1=506.

7C. Preparation of [5-(4-Amino-piperidin-1-ylmethyl)-pyrrolo[2,1-f][1,2,4]triazin-4-yl]-[3-chloro-4-(3-fluoro-benzyloxy)-phenyl]-amine

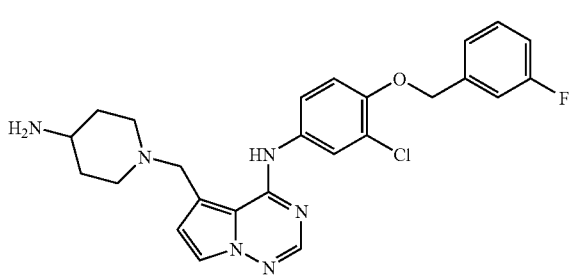

A mixture of the sulfoxide 7B (100 mg, 0.20 mmol) and 4-aminopiperidine (0.6 gm, 6 mmol) was heated in a sealed tube at 135° C. for 4 hr. The reaction mixture was taken up in DCM, washed with water, and dried (Na₂SO₄). Removal of the solvent followed by radial chromatography (2 mm silica gel plate eluted with DCM containing 5% MeOH) afforded 7C (40 mg, 42%) as a foam. Analytical HPLC retention time=1.35 min. (YMC Xterra S7 C18, 3.0×50 mm column, 10–90% aqueous methanol over 2 minutes containing 0.1% TFA, 5 mL/min, monitoring at 220 nm) and a LC/MS M$^+$+1=481.

EXAMPLE 8

[5-(4-Amino-4-methyl-piperidin-1-ylmethyl)-pyrrolo[2,1-f][1,2,4]triazin-4-yl]-[3-chloro-4-(3-fluoro-benzyloxy)-phenyl]-amine

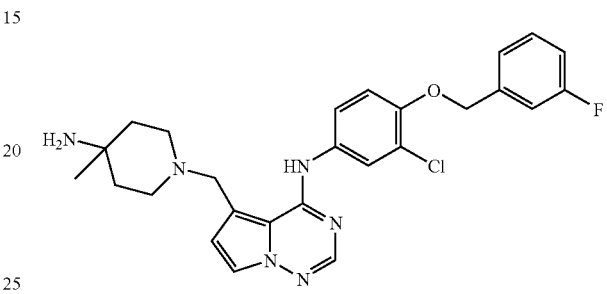

The title compound was prepared from 7B and excess 4-amino-4-methylpiperidine (WO 9732880) by a route analogous to that used for the preparation of 7C. Analytical HPLC retention time=1.43 min. (YMC Xterra S7 C 18, 3.0×50 mm column, 10–90% aqueous methanol over 2 minutes containing 0.1% TFA, 5 mL/min, monitoring at 220 nm) and a LC/MS M$^+$+1=495.

EXAMPLE 9

[3-Chloro-4-(3-fluoro-benzyloxy)-phenyl]-(5-piperazin-1-ylmethyl-pyrrolo[2,1-f][1,2,4]triazin-4-yl)-amine

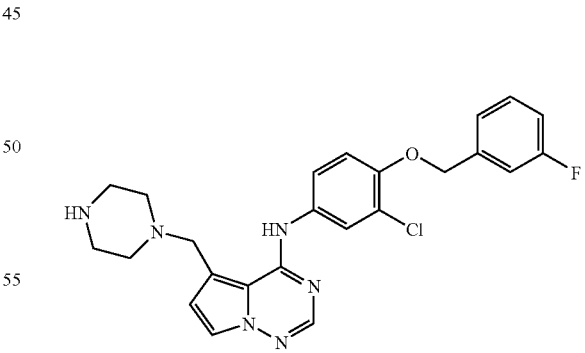

The title compound was prepared from 7B and excess piperazine by a route analogous to that used for the preparation of 7C. Analytical HPLC retention time=1.68 min. (YMC Xterra S7 C18, 3.0×50 mm column, 10–90% aqueous methanol over 2 minutes containing 0.1% TFA, 5 mL/min, monitoring at 220 nm) and a LC/MS M$^+$+1=467.

EXAMPLE 10

[3-Chloro-4-(3-fluoro-benzyloxy)-phenyl]-(5-[1,4]diazepan-1-ylmethyl-pyrrolo[2,1-f][1,2,4]triazin-4-yl)-amine

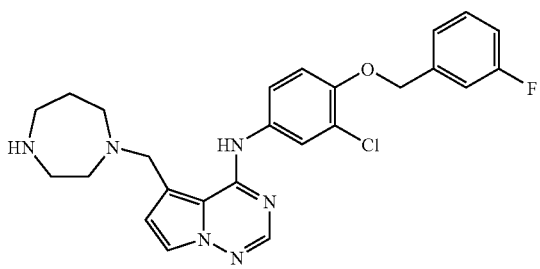

The title compound was prepared from 7B and excess homopiperazine by a route analogous to that used for the preparation of 7C. It had an analytical HPLC retention time=1.36 min. (YMC Xterra S7 C18, 3.0×50 mm column, 10–90% aqueous methanol over 2 minutes containing 0.1% TFA, 5 mL/min, monitoring at 220 nm) and a LC/MS $M^++1=481$.

EXAMPLE 11

5-[(4-Amino-1-piperidinyl)methyl]-N-[3-chloro-4-(1-isoquinolinyl-methoxy)phenyl]pyrrolo[2,1-f][1,2,4]triazin-4-amine, trifluoroacetic acid salt (1:1)

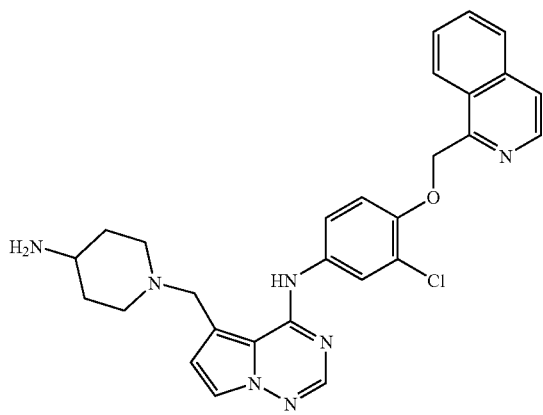

11A. Preparation of 3-chloro-4-(isoquinolin-1-yl-methoxy)-phenylamine

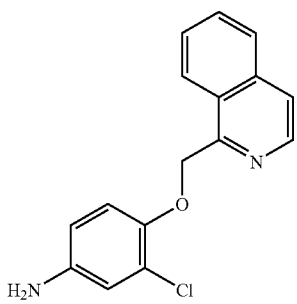

Compound 11A was prepared from 4-amino-2-chlorophenol 1-isoquinolinyl methanol by a route analogous to that used for the preparation of 1C.

11B. Preparation of (1-{4-[3-chloro-4-(isoquinolin-1-ylmethoxy)-phenylamino]-pyrrolo[2,1-f][1,2,4]triazin-5-ylmethyl}-piperidin-4-yl)-carbamic acid tert-butyl ester

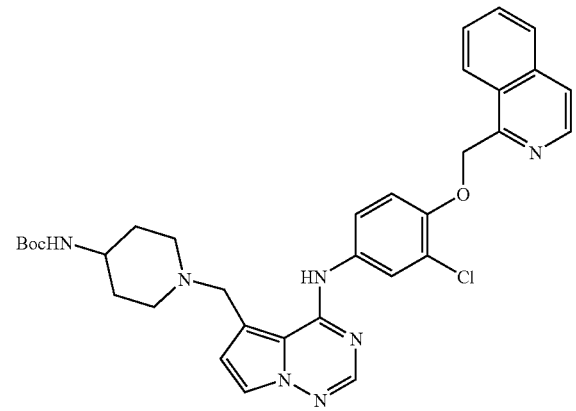

Compound 11B (46.6 mg, 26%) was prepared from 11A (82 mg, 0.29 mmol) and 1E (100 mg, 0.29 mmol) by a route analogous to that used in Method two for the preparation of 1F.

11C. Preparation of 5-[(4-Amino-1-piperidinyl)methyl]-N-[3-chloro-4-(1-isoquinolinylmethoxy)phenyl]pyrrolo[2,1-f][1,2,4]triazin-4-amine, trifluoroacetic acid salt (1:1)

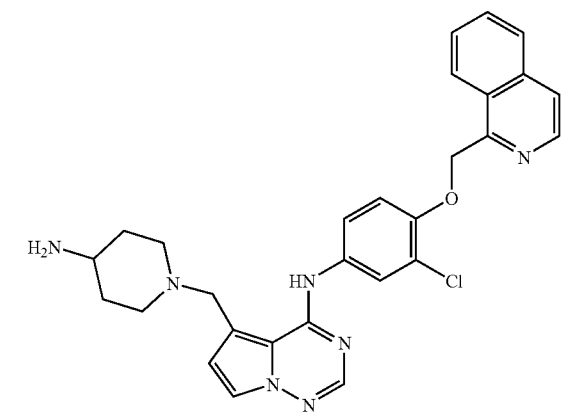

Compound 11C was prepared from 11B by a route analogous to that used for the preparation of 1G. Analytical HPLC retention time=1.79 min. (YMC S5 ODS column 4.6×50 mm, 10–90% aqueous methanol over 4 minutes containing 0.2% phosphoric acid, 4 mL/min, monitoring at 220 nm) and a LC/MS $M^++1=514$

EXAMPLE 12

5-[(4-Amino-1-piperidinyl)methyl]-N-[3-chloro-4-(2-quinolinyl-methoxy)phenyl]pyrrolo[2,1-f][1,2,4]triazin-4-amine, trifluoroacetic acid salt (1:1)

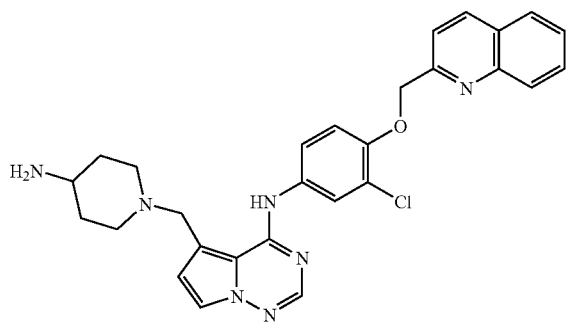

12A. Preparation of 2-(2-chloro-4-nitro-phenoxymethyl)-quinoline

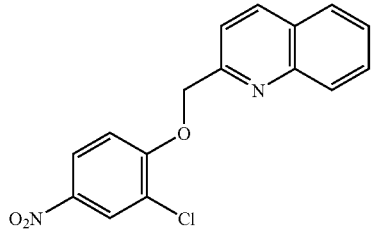

A mixture of 2-chloro-4-nitro-phenol (202 mg, 1.16 mmol), 2-chloromethyl-quinoline hydrochloride (224 mg, 1.04 mmol), K₂CO₃ (354 mg, 2.55 mmol) in CH₃CN (3.6 ml) was heated at 70° C. for 8 h. DMA (2 ml) was added, and the mixture was heated at 80° C. for 4 h. The mixture was cooled to rt, diluted with EtOAc (120 ml), washed with H₂O (6×80 ml) and brine (1×80 ml), dried (MgSO₄) and filtered. The filtrate was concentrated to give 12A (280 mg, 85%).

12B. Preparation of 3-chloro-4-(quinolin-2-ylmethoxy)-phenylamine

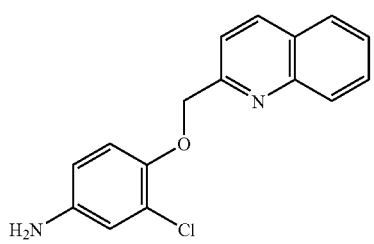

A mixture of 12A (95.5 mg, 0.30 mmol) and Fe powder (135 mg, 2.4 mmol) in HOAc/EtOAc (1/1) (2 ml) was heated at 70° C. for 3.5 h. The mixture was cooled to rt, filtered through an 1" celite pad and rinsed with HOAc/EtOAc (1/1) (4×8 ml). The filtrate was concentrated in vacuo. The residue was diluted with 1N NaOH (40 ml), extracted with EtOAc (2×60 ml) and the combined EtOAc extracts were washed with brine (1×20 ml), dried (MgSO₄), filtered and concentrated in vacuo to give 12B (83.1 mg, 79% pure) which was used in next step without further purification. Analytical HPLC retention time=2.08 min. (YMC Xterra S7 C18, 3.0×50 mm column, 10–90% aqueous methanol over 2 minutes containing 0.1% TFA, 5 mL/min, monitoring at 220 nm).

12C. Preparation of (1-{4-[3-chloro-4-(quinolin-2-yl-methoxy)-phenylamino]-pyrrolo[2,1-f][1,2,4]triazin-5-ylmethyl}-piperidin-4-yl)-carbamic acid tert-butyl ester

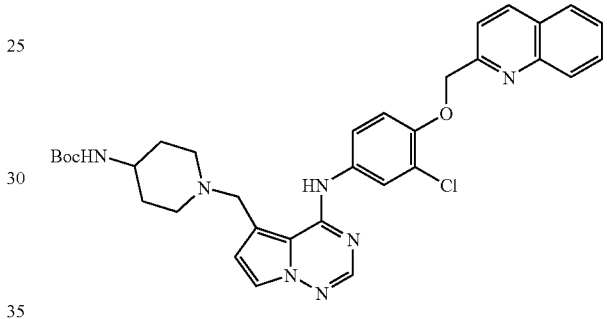

Compound 12C (30 mg, 21%) was prepared from 12B (83.1 mg, 79% pure, 0.23 mmol) and 1E (80.2 mg, 0.23 mmol) by a route analogous to that used in Method two for the preparation of 1F.

12D. Preparation of 5-[(4-Amino-1-piperidinyl)methyl]-N-[3-chloro-4-(2-quinolinyl-methoxy)phenyl]pyrrolo[2,1-f][1,2,4]triazin-4-amine, trifluoroacetic acid salt (1:1).

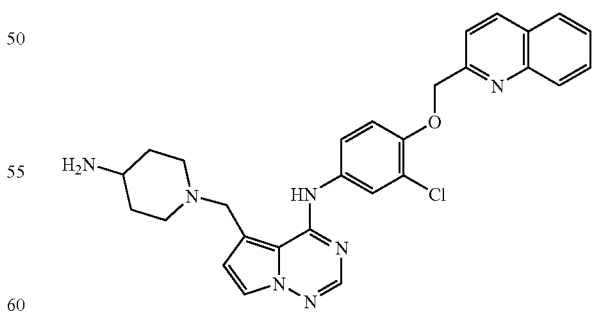

Compound 12D was prepared from 12C by a route analogous to that used for the preparation of 1G. Analytical HPLC retention time=2.4 min. (YMC S5 ODS column 4.6×50 mm, 10–90% aqueous methanol over 4 minutes containing 0.2% phosphoric acid, 4 mL/min, monitoring at 220 nm) and a LC/MS M++1=514

EXAMPLE 13

5-[(4-Amino-piperidin-1-ylmethyl)-pyrrolo[2,1-f][1,2,4]triazin-4-yl]-[6-(3-fluoro-benzyloxy)-pyridin-3-yl]amine

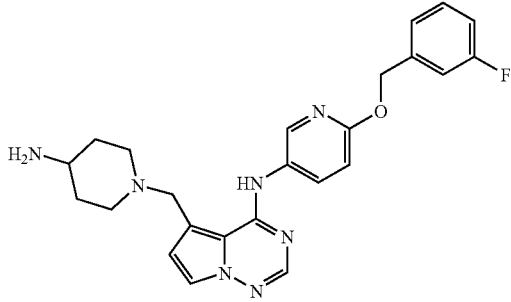

13A. Preparation of 2-(3-Fluoro-benzyloxy)-5-nitro-pyridine

A mixture of 3-flouro-benzyl alcohol (1.07 g, 8.48 mmol), 5-nitro-pyridin-2-ol (1.34 g, 8.48 mmol) and $K_2CO_3$ (1.41 g, 10.2 mmol) in DMA (10 ml) was heated at 120° C. for 7 h. The mixture was cooled to rt, diluted with MeOH(10 ml), filtered and purified by preparative HPLC to give 13A (1.01 g, 48%).

13B. Preparation of 6-(3-Fluoro-benzyloxy)-pyridin-3-ylamine

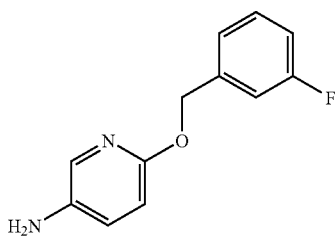

A mixture of 13A (132 mg, 0.53 mmol) and Fe powder (238 mg, 4.25 mmol) in HOAc/EtOAc (1/1) (2.4 ml) was heated at 70° C. for 2.5 h. The mixture was cooled to rt, filtered through a 1" celite pad and rinsed with HOAc/EtOAc (1/1) (4×8 ml). The filtrate was concentrated in vacuo. The residue was diluted with 1N NaOH (25 ml), extracted with EtOAc (2×60 ml) and the combined EtOAc extracts were washed with brine (1×20 ml), dried ($MgSO_4$), filtered and concentrated in vacuo to give 13B (101.7 mg, 78% pure) which was used in the next step without further purification.

13C.

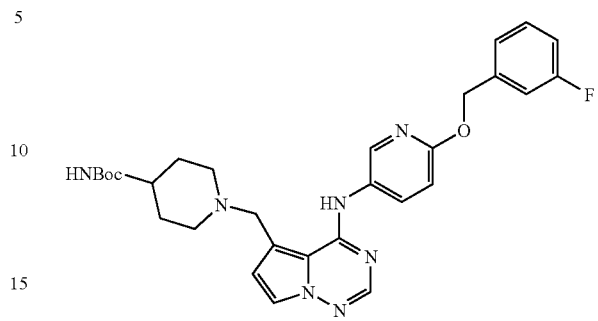

Compound 13C (73 mg, 29%) was prepared from 13B (101.7 mg, 89% pure, 0.36 mmol) and 1E (126.8 mg, 0.36 mmol) by a route analogous to that used in Method two for the preparation of 1F.

13D. Preparation of 5-[[5-[(4-Amino-1-piperidinyl)methyl]pyrrolo[2,1-f][1,2,4]triazin-4-yl]amino]-2-[(3-fluorophenyl)methoxy]benzonitrile, trifluoroacetic acid salt (1:1).

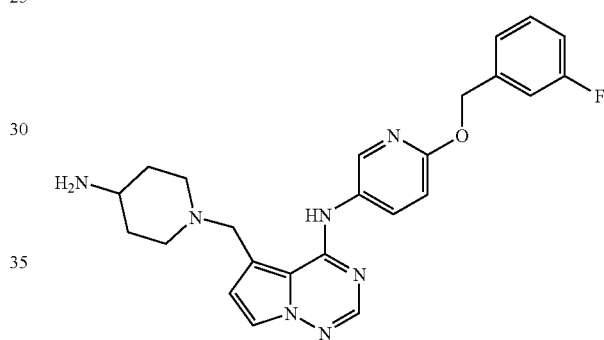

Compound 13D was prepared from 13C by a route analogous to that used for the preparation of 1G. Analytical HPLC retention time=2.13 min. (YMC S5 ODS column 4.6×50 mm, 10–90% aqueous methanol over 4 minutes containing 0.2% phosphoric acid, 4 mL/min, monitoring at 220 nm) and a LC/MS M++1=448

EXAMPLE 14

5-[[5-[(4-Amino-1-piperidinyl)methyl]pyrrolo[2,1-f][1,2,4]triazin-4-yl]amino]-2-[(3-fluorophenyl)methoxy]benzamide, trifluoroacetic acid salt (1:1)

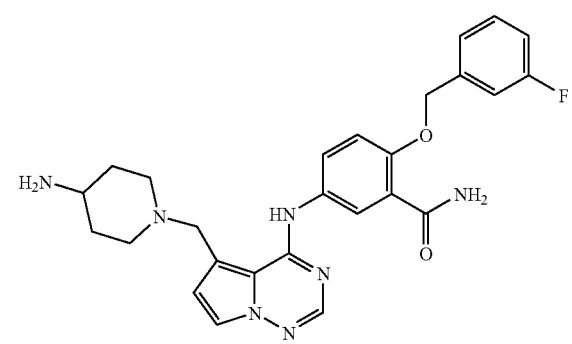

14A. Preparation of 2-(3-Fluoro-benzyloxy)-5-nitro-benzamide

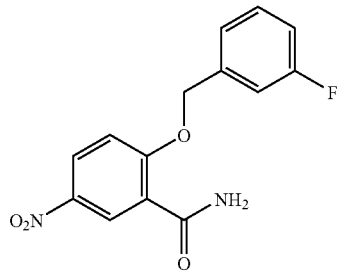

A mixture of 3-flouro-benzyl alcohol (1.0 g, 7.92 mmol), 2-chloro-5-nitro-benzamide (1.59 g, 7.92 mmol) and K₂CO₃ (1.31 g, 9.51 mmol) in DMA (5 ml) was heated at 120° C. for 7 h. The mixture was cooled to rt, diluted with EtOAc(40 ml), filtered and concentrated in vacuo to give 14A (2.0 g, 87%).

14B. Preparation of 5-Amino-2-(3-fluoro-benzyloxy)-benzamide

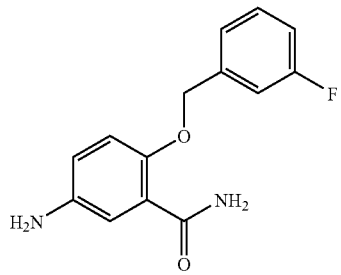

A mixture of 14A (162 mg, 0.56 mmol) and Fe powder (249 mg, 4.46 mmol) in HOAc/EtOAc (1/1) (2.4 ml) was heated at 70° C. for 2.5 h. The mixture was cooled to rt, filtered through a 1" celite pad and rinsed with HOAc/EtOAc (1/1) (4×8 ml). The filtrate was concentrated in vacuo. The residue was diluted with 1N NaOH (25 ml), extracted with EtOAc (2×60 ml) and the combined EtOAc extracts were washed with brine (1×20 ml), dried (MgSO₄), filtered and concentrated in vacuo to give 14B (123.8 mg, 67% pure).

14C.

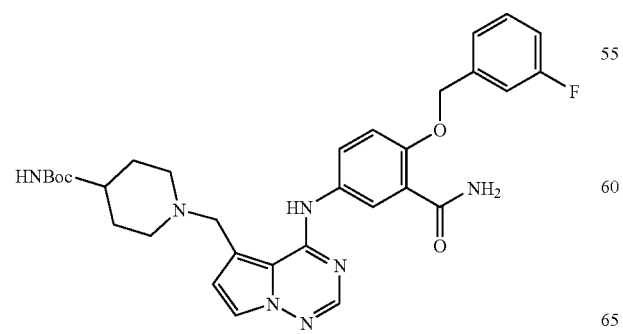

Compound 14C (100 mg, 45%) was prepared from 14B (123.8 mg, 79% pure, 0.38 mmol) and 1E (130.6 mg, 0.38 mmol) by a route analogous to that used in Method two for the preparation of 1F.

14D. Preparation of 5-[[5-[(4-Amino-1-piperidinyl)methyl]pyrrolo[2,1-f][1,2,4]triazin-4-yl]amino]-2-[(3-fluorophenyl)methoxy]benzamide, trifluoroacetic acid salt (1:1).

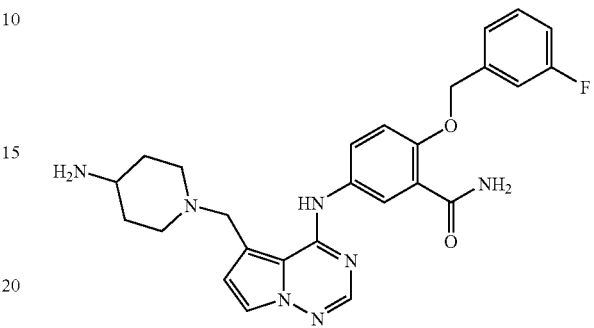

Compound 14D was prepared from 14C by a route analogous to that used for the preparation of 1G. Analytical HPLC retention time=1.93 min. (YMC S5 ODS column 4.6×50 mm, 10–90% aqueous methanol over 4 minutes containing 0.2% phosphoric acid, 4 mL/min, monitoring at 220 nm) and a LC/MS M⁺+1=490

EXAMPLE 15

5-[(4-Amino-1-piperidinyl)methyl]-N-[3-chloro-4-[(6-methyl-2-pyridinyl)-methoxy]phenyl]-pyrrolo[2,1-f][1,2,4]triazin-4-amine, trifluoroacetic acid salt (1:1)

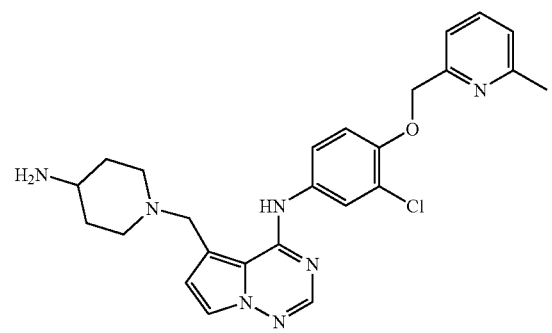

15A. Preparation of 3-Chloro-4-(6-methyl-pyridin-2-yl-methoxy)-phenylamine

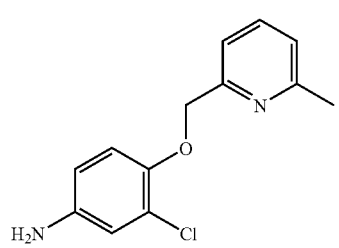

To a mixture of (6-methyl-pyridin-2-yl)-methanol (280 mg, 2.29 mmol), 4-amino-2-chloro-phenol (359 mg, 2.5 mmol) and triphenylphosphine (0.655 mg, 2.5 mmol) in THF (8 ml) was added DIAD (0.49 ml, 2.5 mmol) and the mixture was stirred at rt for 20 h. The mixture was concentrated in vacuo, diluted with 1N HCl (30 ml), washed with EtOAc (3×20 ml) and basified to pH 12 by 1N NaOH. The mixture was extracted with EtOAc (4×40 ml); the combined EtOAc extracts were washed with brine (1×20 ml), dried (MgSO₄), filtered and concentrated in vacuo to give 15A (?? mg, ??% pure)

15B.

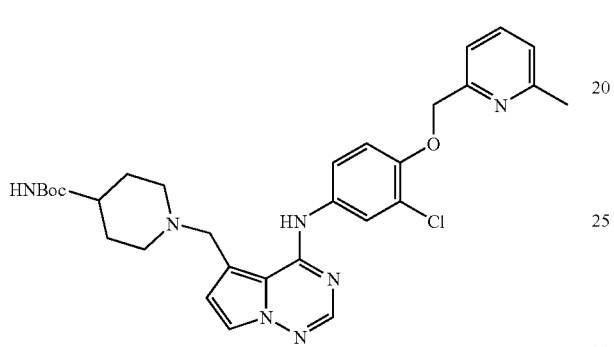

Compound 15B (42 mg, 25%) was prepared from 15A (71.5 mg, 0.29 mmol) and 1E (100 mg, 0.29 mmol) by a route analogous to that used in Method two for the preparation of 1F.

15C. Preparation of 5-[(4-Amino-1-piperidinyl)methyl]-N-[3-chloro-4-[(6-methyl-2-pyridinyl)-methoxy]phenyl]-pyrrolo[2,1-f][1,2,4]triazin-4-amine, trifluoroacetic acid salt (1:1).

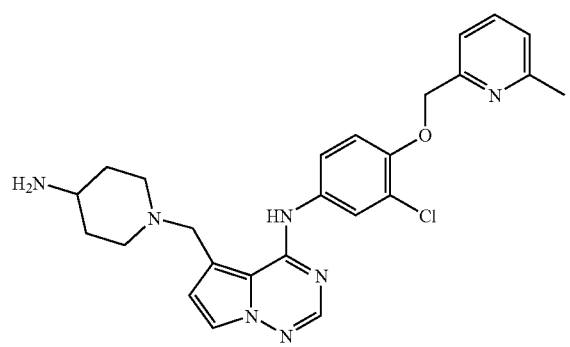

Compound 15C was prepared from 15B by a route analogous to that used for the preparation of 1G. Analytical HPLC retention time=1.39 min. (YMC S5 ODS column 4.6×50 mm, 10–90% aqueous methanol over 4 minutes containing 0.2% phosphoric acid, 4 mL/min, monitoring at 220 nm) and a LC/MS M⁺+1=478.

EXAMPLE 16

5-[(4-Amino-1-piperidinyl)methyl]-N-[3-chloro-4-(pyrazinylmethoxy)-phenyl]pyrrolo[2,1-f][1,2,4]triazin-4-amine, trifluoroacetic acid salt (1:1)

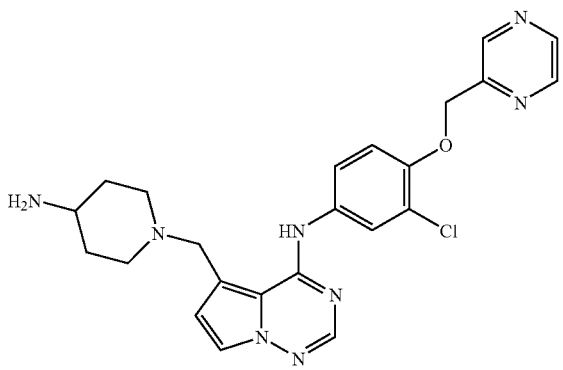

16A. Preparation of 3-chloro-4-(pyrazin-2-ylmethoxy)-phenylamine

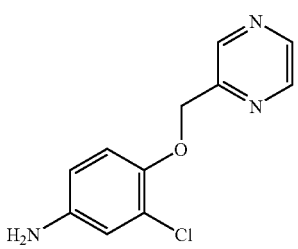

To a mixture of pyrazin-2-yl-methanol (62 mg, 0.56 mmol), 4-amino-2-chloro-phenol (80.8 mg, 0.56 mmol) and triphenylphosphine (148 mg, 0.56 mmol) in THF (3 ml) was added DIAD (0.11 ml, 0.56 mmol) and the mixture was stirred at rt for 20 h. The mixture was concentrated in vacuo, diluted with 1N HCl (30 ml), washed with EtOAc (3×20 ml) and basified to pH 12 by 1N NaOH. The mixture was extracted with EtOAc (4×40 ml) and the combined EtOAc extracts were washed with brine (1×20 ml), dried (MgSO₄), filtered and concentrated in vacuo to give 16A (43.3 mg, 33% pure)

16B.

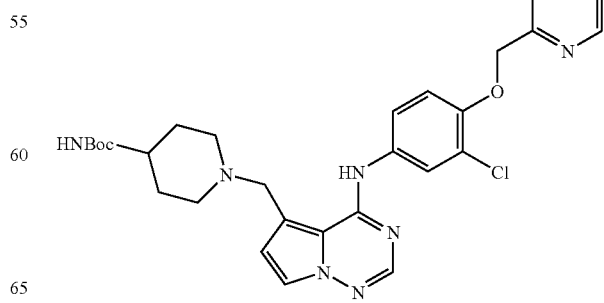

Compound 16B (58 mg, 55.5%) was prepared from 16A (43.3 mg, 0.18 mmol) and 1E (64 mg, 0.18 mmol) by a route analogous to that used in Method two for the preparation of 1F.

16C. Preparation of 5-[(4-amino-1-piperidinyl)methyl]-N-[3-chloro-4-(pyrazinylmethoxy)phenyl]pyrrolo[2,1-f][1,2,4]triazin-4-amine, trifluoroacetic acid salt (1:1).

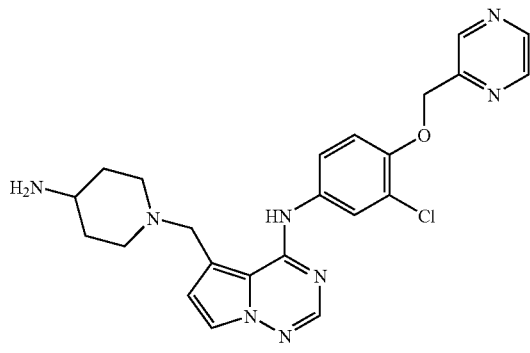

Compound 16C was prepared from 16B by a route analogous to that used for the preparation of 1G. Analytical HPLC retention time=1.7 min. (YMC S5 ODS column 4.6×50 mm, 10–90% aqueous methanol over 4 minutes containing 0.2% phosphoric acid, 4 mL/min, monitoring at 220 nm) and a LC/MS $M^++1=465$

EXAMPLE 17

5-[[(3R,4S)-rel-4-Amino-3-methyl-1-piperidinyl]methyl]-N-[3-chlor-4-(2-pyridinylmethoxy)phenyl]pyrrolo[2,1-f][1,2,4]triazin-4-amine, trifluoroacetic acid salt (1:1)

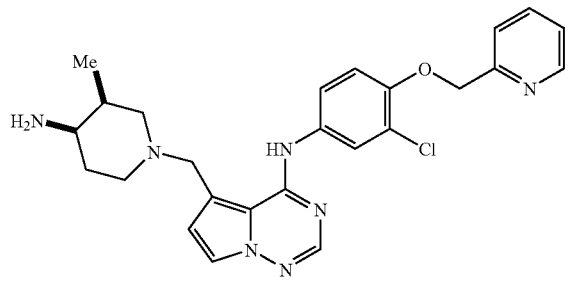

A solution of benzylidene-(3-methyl-piperidin-4-yl)-amine (30 mg, 0.15 mmol) in acetonitrile (2.5 mL) was treated with {4-[3-chloro-4-(pyridin-2-ylmethoxy)-phenylamino]-pyrrolo[2,1-f][1,2,4]triazin-5-ylmethyl}-triethylammonium bromide (86 mg, 0.15 mmol) and diisopropylethylamine (10 µL, 0.15 mmol). The resulting solution was warmed to 50° C. for one hour and monitored by HPLC. Upon completion, the reaction mixture was cooled to room temperature and concentrated to an amber oil. Reversed-phase preparative HPLC (YMC ODS-A 5 uM 20×100 mm, 10% to 90% aqueous methanol containing 0.1% TFA gradient over 15 min) followed by radial chromatography (2 mm plate, 10% MeOH/CH$_2$Cl$_2$) afforded the desired compound as a trifluoroacetic acid salt (10 mg, 11%). LC/MS (M+H)=478, HPLC $t_R$=1.663 min (YMC S5 ODS 4.6×50 mm, 10–90% aqueous methanol, 4 min gradient, monitored at 220 nm)

EXAMPLE 18

[[3-Chloro-4-(3-fluoro-benzyloxy)-phenyl]-(5-methanesulfinylmethyl-pyrrolo[2,1-f][1,2,4]triazin-4-yl)-amine

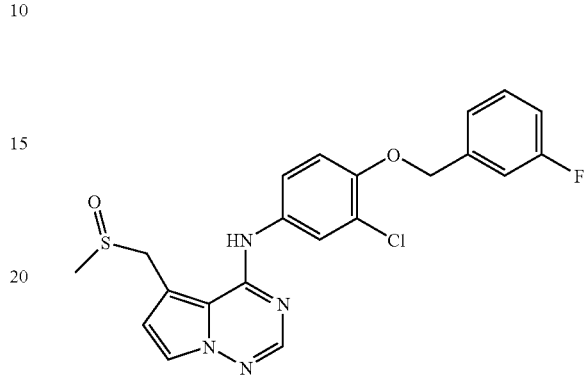

A solution of 5-bromomethyl-4-chloro-pyrrolo[2,1-f][1,2,4]triazine (1 gm, 4.05 mmole) in DCM (40 mL) was sparged with N$_2$ for 15 min. The solution was cooled in an ice bath and thiolacetic acid (0.319 mL, 1.1 equiv) and DIPEA (0.71 mL, 1 equiv) were added. After 0.5 h, the reaction was removed from the bath and after an additional 0.5 h, it was washed with water (3×), dried (Na$_2$SO$_4$), and the solvent was removed. The crude thioacetic acid S-(4-chloro-pyrrolo[2,1-f][1,2,4]triazin-5-ylmethyl) ester and 3-chloro-4-(3-fluoro-benzyloxy)-phenylamine (0.915 mg, 0.9 equiv) were dissolved in a mixture of 1,2-dichloroethane (4 mL) and n-butanol (4 mL) and heated at 85° C. for 1 h. The solvents were removed and the residue was partitioned between DCM and sat. aq. NaHCO$_3$ solution. The organic phase was separated, washed with water, dried (Na$_2$SO$_4$), and the solvent removed. Radial chromatography (silica gel plate eluted with DCM containing 0, 0.5, 1% MeOH) afforded thioacetic acid S-{4-[3-chloro-4-(3-fluoro-benzyloxy)-phenylamino]-pyrrolo[2,1-f][1,2,4]triazin-5-ylmethyl} ester (986 mg, 54%). A portion of this thioester (120 mg, 0.263 mmole) was dissolved in dry THF and sparged with N$_2$ for 15 min. NaOMe (0.525 mL of a 0.5 M solution of NaOMe in MeOH, 1.1 equiv) and MeI (0.016 mL) were added with stirring. After 0.5 h, the solvents were removed and the residue was partitioned between DCM and water. The organic phase was separated, dried (Na$_2$SO$_4$), and the solvent was removed. Purification by radial chromatography (silica gel plate eluted with DCM containing 0, 0.5, 1% MeOH) afforded [3-chloro-4-(3-fluoro-benzyloxy)-phenyl]-(5-methylsulfanyl-methyl-pyrrolo[2,1-f][1,2,4]triazin-4-yl)-amine (91 mg, 81%): $^1$H NMR (CDCl$_3$) δ 2.26 (s, 3H), 4.06 (s, 2H), 5.19 (s, 2H), 6.57 (d, 1H, J=2.6 Hz), 6.95–7.93 (m, 10H), 8.86 (s, 1H). Solid m-chloroperbenzoic acid (54 mg, 58 to 70%, 1 equiv) was added to an ice-cooled solution of the thioether (91 mg, 0.21 mmole) in CHCl$_3$. After 1 h, this was removed from the bath and washed with a 6% aq. solution of NaHSO$_3$ and sat. aq. NaHCO$_3$ (3×) and then dried (Na$_2$SO$_4$). Radial chromatography (silica gel plate eluted with the DCM containing 0, 0.5, 1, 2, 3% MeOH) afforded the title compound (49 mg, 51%): MS: 445 (M+H)$^+$; HPLC Ret Time: 1.70 min (YMC Xterra C18 S7, 3.0×50 mm column, 2 min gradient, 5 mL/min).

EXAMPLE 19

2-{4-[3-Chloro-4-(3-fluoro-benzyloxy)-phenylamino]-pyrrolo[2,1-f][1,2,4]triazin-5-ylmethanesulfinyl}-ethanol

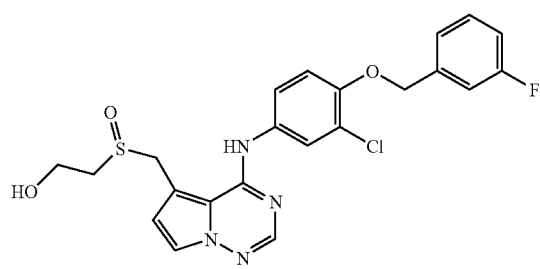

A solution of thioacetic acid S-{4-[3-chloro-4-(3-fluorobenzyloxy)-phenylamino]-pyrrolo[2,1-f][1,2,4]triazin-5-ylmethyl}ester (80 mg, 0.175 mmole) in dry THF (4 mL) was sparged with $N_2$ for 15 min. NaOMe (0.40 mL, 0.5 M in MeOH, 1.1 equiv), 2-bromoethanol (0.013 mL, 1 equiv) were added and the reaction was left stirring at RT. After 16 h, the solvents were removed and the residue was partitioned between DCM and water. The organic phase was separated, dried ($Na_2SO_4$), and the solvent removed. Radial chromatography (silica gel plate eluted with DCM containing 0, 0.5, 1, 2% MeOH) afforded 2-{4-[3-chloro-4-(3-fluoro-benzyloxy)-phenylamino]-pyrrolo[2,1-f][1,2,4]triazin-5-ylmethylsulfanyl}-ethanol (35 mg, 44%): $^1$H NMR (CDCl$_3$) δ 2.73 (t, 2H, J=5.9 Hz), 3.81 (t, 2H, J=5.9 Hz), 4.11 (s, 2H), 5.13 (s, 2H), 6.55 (d, 1H, J=2.6 Hz), 6.92–7.93 (m, 10H), 8.99 (s, 1H). Solid m-chloroperbenzoic acid (19 mg, 58 to 70%, 1 equiv) was added to an ice-cooled solution of the alcohol (35 mg, 0.18 mmole) in CHCl$_3$ (4 mL). After 1 h, this was removed from the bath and washed with a 6% aq. solution of NaHSO$_3$, sat. aq. NaHCO$_3$ (3×) and then dried (Na$_2$SO$_4$). Radial chromatography (silica gel plate eluted with DCM containing 0, 0.5, 1, 2, 3% MeOH) afforded the title compound (22 mg, 60%): MS: 475 (M+H)$^+$; HPLC Ret Time: 1.66 min (YMC Xterra C18 S7, 3.0×50 mm column, 2 min gradient, 5 mL/min).

EXAMPLE 20

5-[[5-[(4-Amino-1-piperidinyl)methyl]pyrrolo[2,1-f][1,2,4]triazin-4-yl]amino]-2-[(3-fluorophenyl)methoxy]benzonitrile, trifluoroacetic acid salt (1:1)

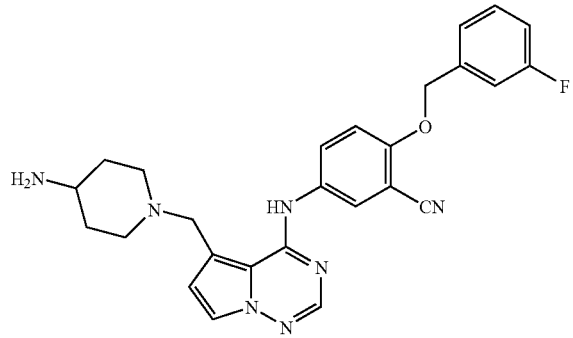

20A. Preparation of 2-(3-fluoro-benzyloxy)-5-nitro-benzonitrile

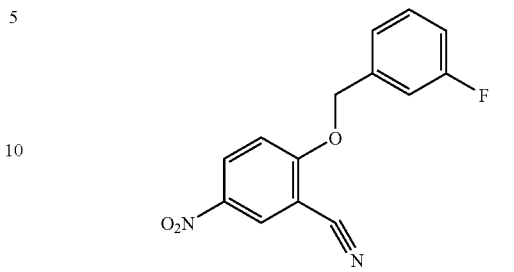

A mixture of 2-fluoro-5-nitro-benzonitrile (290 m g, 1.74 mmol), 3-flouro-benzyl alcohol (1220 mg, 1.74 mmol) and K$_2$CO$_3$ (219 mg, 2.09 mmol) in DMA (4 ml) was heated at 120° C. for 7 h. The mixture was cooled to rt, diluted with MeOH(10 ml), filtered and purified by preparative HPLC to give 20A (380 mg, 80%).

20B. Preparation of 5-amino-2-(3-fluoro-benzyloxy)-benzonitrile

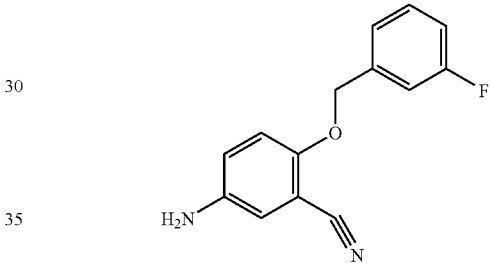

A mixture of 20A (108 mg, 0.4 mmol) and tin chloride (268 mg ,1.2 mmol) in EtOAc (4 ml) was heated to reflux for 15 h. The mixture was cooled to rt and triturated with EtOAc (2×60 ml). The filtrate was concentrated in vacuo. The combined EtOAc extracts were washed with NaHCO$_3$ (1×30 ml), brine (1×30 ml), dried (MgSO$_4$), filtered and concentrated in vacuo to give 20B (43 mg, 45% pure) which was used in next step without further purification.

20C.

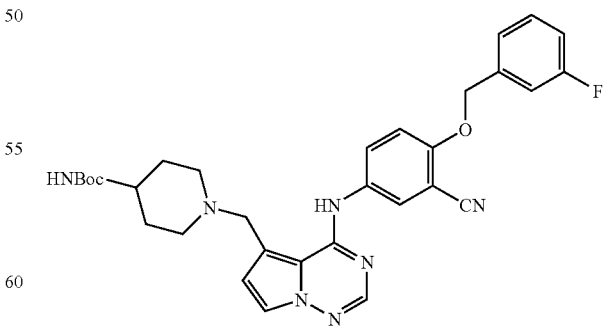

Compound 20C (21 mg, 21%) was prepared from 20B(43 mg, 0.18 mmol) and 1E (62 mg, 0.18mmol) by a route analogous to that used in Method two for the preparation of 1F.

20D Preparation of 5-[[5-[(4-Amino-1-piperidinyl)methyl]pyrrolo[2,1-f][1,2,4]triazin-4-yl]amino]-2-[(3-fluorophenyl)methoxy]benzonitrile, trifluoroacetic Acid Salt (1:1).

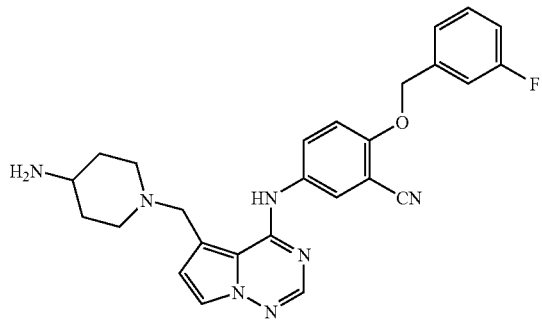

Compound 20D was prepared from 20C by a route analogous to that used for the preparation of 1G. Analytical HPLC retention time=2.15 min. (YMC S5 ODS column 4.6×50 mm, 10–90% aqueous methanol over 4 minutes containing 0.2% phosphoric acid, 4 mL/min, monitoring at 220 nm) and a LC/MS M⁺+1=472

EXAMPLE 21

[5-(4-Amino-piperidin-1-ylmethyl)-pyrrolo[2,1-f][1,2,4]triazin-4-yl]-[3-chloro-4-(pyridin-4-ylmethoxy)-phenyl]-amine

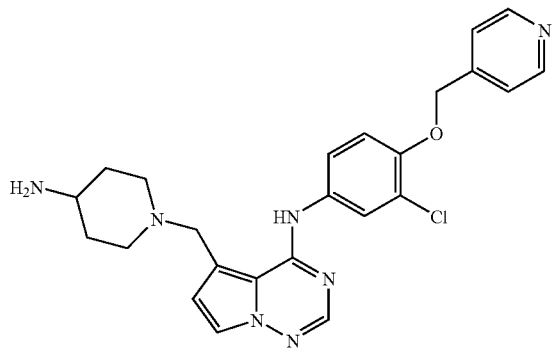

21A. Preparation of {1-[4-(3-Chloro-4-hydroxy-phenylamino)-pyrrolo[2,1-f][1,2,4]triazin-5-ylmethyl]-piperidin-4-yl}-carbamic acid, tert-butyl ester

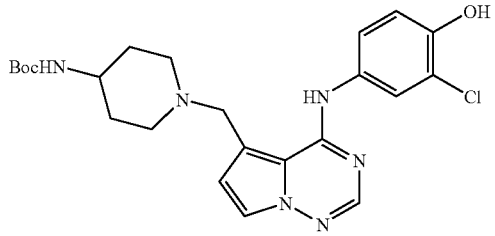

Compound 21A (2.5 g) was prepared from 1E (2.5 g, 7.2 mmol), 4-amino-2-chlorophenol (1.03 g, 7.2 mmol) and piperidine-4-yl-carbamic acid tert-butyl ester (1.44 g, 7.2 mmol) in acetonitrile by a route analogous to that used in Method Two for the preparation of 1F. Analytical HPLC retention time=2.436 min. (Chromolith Speed ROD column 4.6×50 mm, 10–90% aqueous methanol over 4 minutes containing 0.2% trifluoroacetic acid, 4 mL/min, monitoring at 254 nm) and a LC/MS M⁺+1=473⁺.

21B. Preparation of (1-{4-[3-Chloro-4-(pyridin-4-ylmethoxy)-phenylamino]-pyrrolo[2,1-f][1,2,4]triazin-5-ylmethyl}-piperidin-4-yl)-carbamic acid, tert-butyl ester

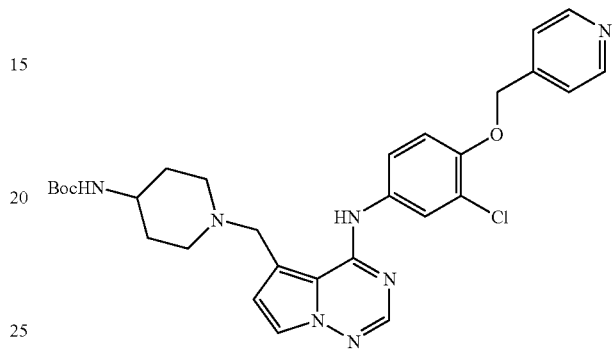

To a mixture of 21A (0.047 g, 0.1 mmol), triphenylphosphine (79 mg, 0.3 mmol), and 4-hydroxymethylpyridine (22 mg, 0.2 mmol) in dry THF was added diethyl azodicarboxylate (0.047 ml, 0.3 mmol). The mixture was stirred at room temperature overnight and purified by preparative HPLC to give Compound 21B as a colorless semi-solid (TFA salt). Analytical HPLC retention time=2.303 min. (Chromolith Speed ROD column 4.6×50 mm, 10–90% aqueous methanol over 4 minutes containing 0.2% trifluoroacetic acid, 4 mL/min, monitoring at 254 nm) and a LC/MS M⁺+1=564⁺.

21C. Preparation of [5-(4-Amino-piperidin-1-ylmethyl)-pyrrolo[2,1-f][1,2,4]triazin-4-yl]-[3-chloro-4-(pyridin-4-ylmethoxy)-phenyl]-amine

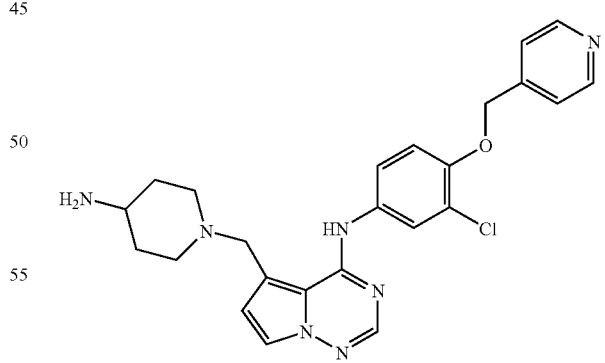

Compound 21C (31 mg) was prepared from 21B by a route analogous to that used for the preparation of 1G as a white solid. Analytical HPLC retention time=1.480 min. (Chromolith Speed ROD column 4.6×50 mm, 10–90% aqueous methanol over 4 minutes containing 0.2% trifluoroacetic acid, 4 mL/min, monitoring at 254 nm) and a LC/MS M⁺+1=464⁺.

EXAMPLES 22–30

Compounds 22–30 were prepared from Compound 21A (0.047 mg, 0.1 mmol) and corresponding alcohols (0.1 mmol) by a route analogous to that used for the preparation of Example 21.

TABLE 1

| Ex. No | Ar | Compound name | HPLC time (min) | (M + H)⁺ |
|---|---|---|---|---|
| 22 | 5-methyl-pyridin-3-yl | [5-(4-Amino-piperidin-1-ylmethyl)-pyrrolo[2,1-f][1,2,4]triazin-4-yl]-[3-chloro-4-(5-methyl-pyridin-3-ylmethoxy)-phenyl]-amine | 1.26 | 478 |
| 23 | 5-fluoro-pyridin-3-yl | [5-(4-Amino-piperidin-1-ylmethyl)-pyrrolo[2,1-f][1,2,4]triazin-4-yl]-[3-chloro-4-(5-fluoro-pyridin-3-ylmethoxy)-phenyl]-amine | 2.16 | 482 |
| 24 | 6-methyl-pyridin-3-yl | [5-(4-Amino-piperidin-1-ylmethyl)-pyrrolo[2,1-f][1,2,4]triazin-4-yl]-[3-chloro-4-(6-methyl-pyridin-3-ylmethoxy)-phenyl]-amine | 1.56 | 478 |
| 25 | 2-methyl-pyridin-3-yl | [5-(4-Amino-piperidin-1-ylmethyl)-pyrrolo[2,1-f][1,2,4]triazin-4-yl]-[3-chloro-4-(2-methyl-pyridin-3-ylmethoxy)-phenyl]-amine | 1.53 | 478 |
| 26 | 4-methyl-pyridin-3-yl | [5-(4-Amino-piperidin-1-ylmethyl)-pyrrolo[2,1-f][1,2,4]triazin-4-yl]-[3-chloro-4-(4-methyl-pyridin-3-ylmethoxy)-phenyl]-amine | 1.51 | 478 |

TABLE 1-continued

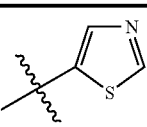

| Ex. No | Ar | Compound name | HPLC time (min) | (M + H)+ |
|---|---|---|---|---|
| 27 | 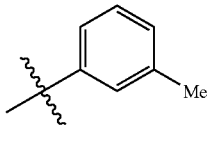 | [5-(4-Amino-piperidin-1-yl-methyl)-pyrrolo[2,1-f][1,2,4]triazin-4-yl]-[3-chloro-4-(thiazol-5-ylmethoxy)-phenyl]-amine | 1.92 | 470 |
| 28 | 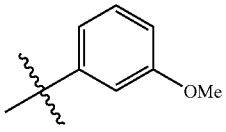 | | 2.79 | 477 |
| 29 | 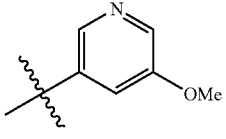 | | 2.57 | 493 |
| 30 | | | 1.63 | 494 |

EXAMPLE 31

[5-(4-Amino-piperidin-1-ylmethyl)-pyrrolo[2,1-f][1,2,4]triazin-4-yl]-[3-chloro-4-(6-methyl-pyrazin-2-ylmethoxy)-phenyl]-amine

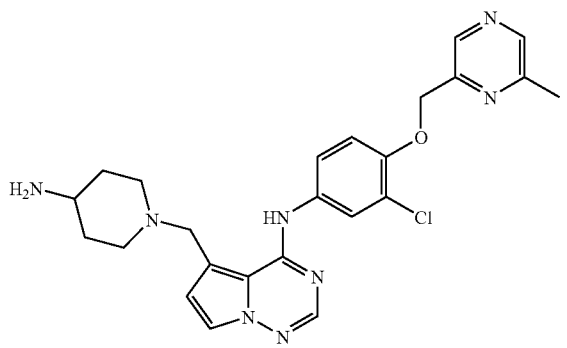

31A. Preparation of 3-Chloro-4-(6-methyl-pyrazin-2-yl-methoxy)-phenylamine

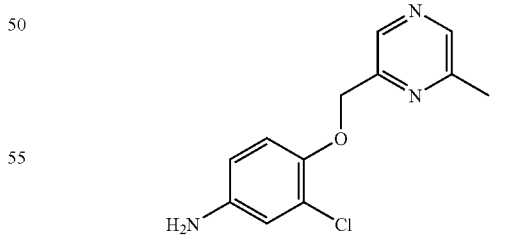

Compound 31A was prepared by a route analogous to that used for the preparation of Compound 16A. Analytical HPLC retention time=1.593 min. (Chromolith Speed ROD column 4.6×50 mm, 10–90% aqueous methanol over 4 minutes containing 0.2% trifluoroacetic acid, 4 mL/min, monitoring at 254 nm) and a LC/MS M+ +1=250+.

31B. Preparation of [5-(4-Amino-piperidin-1-ylmethyl)-pyrrolo[2,1-f][1,2,4]triazin-4-yl]-[3-chloro-4-(6-methyl-pyrazin-2-ylmethoxy)-phenyl]-amine

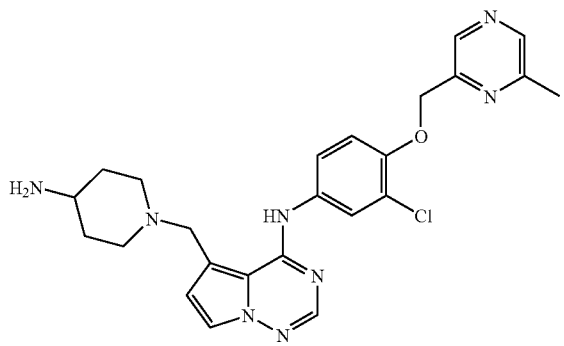

Compound 31B was prepared from 1E (613 mg, 1.76 mmol) and 31A (440 mg, 1.76 mmol) by a route analogous to that used in Method Two for the preparation of Compound 1F. Analytical HPLC retention time=2.016 min. (Chromolith Speed ROD column 4.6×50 mm, 10–90% aqueous methanol over 4 minutes containing 0.2% trifluoroacetic acid, 4 mL/min, monitoring at 254 nm) and a LC/MS $M^++1=479^+$.

EXAMPLE 32

4-Amino-1-{4-[3-chloro-4-(pyridin-2-ylmethoxy)-phenylamino]-pyrrolo[2,1-f][1,2,4]triazin-5-yl-methyl}-piperidin-3-ol (Enantiomer A)

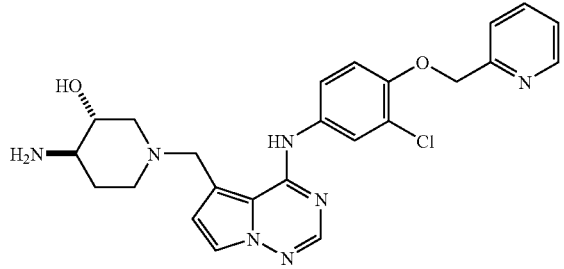

32A. Preparation of 4-Azido-piperidin-3-ol (racemate):

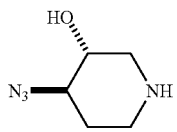

A solution of 3,6-dihydro-2H-pyridine-1-carboxylic acid tert-butyl ester (7.36 g, 40.2 mmol), prepared according to literature [Heterocycles, 1994, 39 (1), 163–170)], in dry $CH_2Cl_2$ (80 mL) was treated with m-CPBA (13 g, 56.3 mmol) in dry $CH_2Cl_2$ (160 mL) overnight. The reaction mixture was washed with sat'd $Na_2S_2O_3$, $NaHCO_3$ and brine and dried over anhydrous $Na_2SO_4$ to give, after removal of solvent under reduced pressure, 8.02 g of epoxide as a light orange oil which was used directly in the next step reaction without further purification. To a solution of 8.02 g of epoxide in 80 mL of dry DMF was added a solution of $NaN_3$ (3.92 g, 60.3 mmol) in a 2:1 acetone-water (80 mL). The mixture was heated at 80° C. overnight. After cooled to room temperature, EtOAc (300 mL) and water (200 mL) were added and the organic layer was separated and washed with 10% LiCl solution (×2), followed by sat'd $NaHCO_3$, brine and dried over anhydrous $Na_2SO_4$. The solvent was evaporated under reduced pressure and the residue was purified by flash chromatography (Hexane-EtOAc: 8.5:1.5 to 1:1) on silica gel to give 5.27 g (54%) of azido alcohol as a white crystalline material. The structure of this azido alcohol was confirmed by a single X-ray crystallographic analysis. To a solution of the aforementioned azido alcohol (0.6 g, 2.48 mmol) in dry $CH_2Cl_2$ (5 mL) at 0° C. was added TFA (5 mL) and the reaction mixture was stirred at ambient temperature for 3 hr. Evaporation under reduced pressure to remove volatile material, the residue was dissolved in EtOAc (20 mL) and washed with sat'd $NaHCO_3$. The aqueous layer was supersaturated with solid NaCl and back extracted with EtOAc (20 mL×10). The combined organic extracts were dried over anhydrous $Na_2SO_4$ and the solvent was evaporated under reduced pressure to give 0.350 g of Compound 32A as a yellow oil which was used directly in next step reaction with out further purification. $^1$H-NMR ($CDCl_3$+$CD_3OD$): δ 3.58 (m, 1H), 3.44 (m, 1H), 3.18 (m, 1H), 3.05 (m, 1H), 2.75 (m, 1H), 2.65 (m, 1H), 2.10 (m, 1H), 1.57 (m, 1H).

32B. Preparation of 4-Azido-1-{4-[3-chloro-4-(pyridin-2-ylmethoxy)-phenylamino]pyrrolo[2,1-f][1,2,4]triazin-5-yl-methyl}-piperidin-3-ol (racemate):

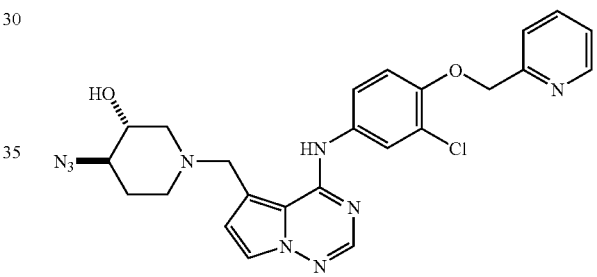

Compound 32B was prepared from 1C (117 mg, 0.5 mmol), 1E (174 mg, 0.5 mmol) and 32A (71 mg, 0.5 mmol) by a route analogous to that used in Method Two for the preparation of Compound 1F, substituting piperidin-4-yl-carbamic acid tert-butyl ester with Compound 32A. Analytical HPLC retention time=1.883 min. (Chromolith Speed ROD column 4.6×50 mm, 10–90% aqueous methanol over 4 minutes containing 0.2% trifluoroacetic acid, 4 mL/min, monitoring at 254 nm) and a LC/MS $M^++1=506^+$.

32C. Preparation of 4-Amino-1-{4-[3-chloro-4-(pyridin-2-ylmethoxy)phenylamino]pyrrolo[2,1-f][1,2,4]triazin-5-yl-methyl}-piperidin-3-ol (racemate)

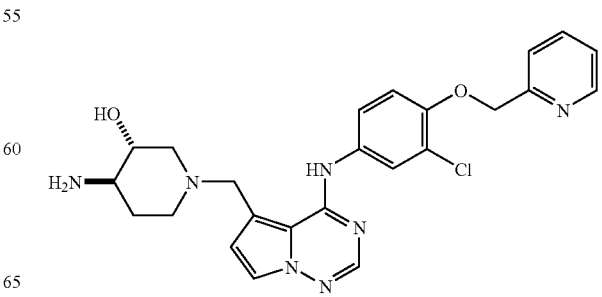

A mixture of Compound 32B (0.5 mmol, crude) and PPh₃ (262 mg, 1.25 mmol) in THF (5 mL) and water (0.05 mL) was heated to reflux for 6 hr. After cooling, the reaction mixture was concentrated under reduced pressure and the residue was purified by flash chromatography (CH₂Cl₂—MeOH—NH₄OH: 95:5:0.5) on silica gel to give 160 mg of Compound 32C as a white solid. Analytical HPLC retention time=1.599 min. (Chromolith Speed ROD column 4.6×50 mm, 10–90% aqueous methanol over 4 minutes containing 0.2% trifluoroacetic acid, 4 mL/min, monitoring at 254 nm) and a LC/MS M⁺+1=480⁺.

32D. Preparation of 4-Amino-1-{4-[3-chloro-4-(pyridin-2-ylmethoxy)phenylamino]pyrrolo[2,1-f][1,2,4]triazin-5-yl-methyl}-piperidin-3-ol (enantiomer A)

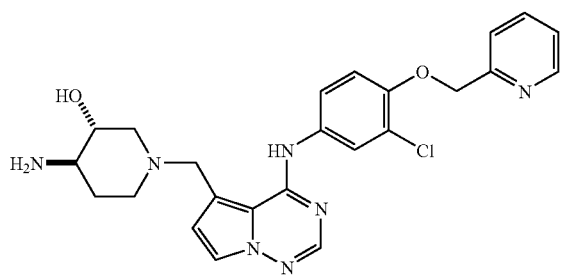

Compound 32D was obtained from Compound 32C using a chiral HPLC separation technique [Chiralpak AD, 250×4.6 mm, 10 micron, 250 nm detection, using hexane/isopropanol/MeOH/diethyl amine (50:25:25:0.05) as the mobile phase]. The first eluent (Rt. 7.730 min) was collected and the solvents were removed under reduced pressure to give, after drying under high vacuum, 26.4 mg of Compound 32D as a white solid (with 98.5% ee). Analytical HPLC retention time and LC/MS are identical to its racemate, Compound 32C.

EXAMPLE 33

4-Amino-1-{4-[3-chloro-4-(pyridin-2-ylmethoxy)-phenylamino]-pyrrolo[2,1-f][1,2,4]triazin-5-yl-methyl}-piperidin-3-ol (Enantiomer B)

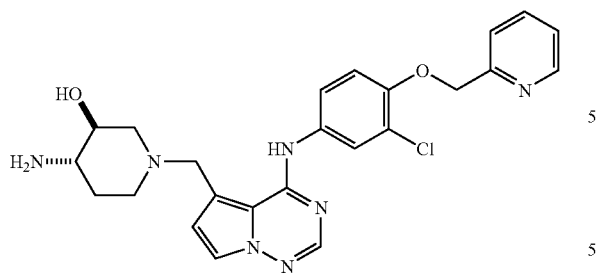

Compound 33 was obtained from Compound 32C following the same procedure using a chiral HPLC separation technique [Chiralpak AD, 250×4.6 mm, 10 micron, 250 nm detection, using hexane/isopropanol/MeOH/diethyl amine (50:25:25:0.05) as the mobile phase]. The second eluent (Rt. 9.724 min) was collected and the solvents were removed under reduced pressure to give, after drying under high vacuum, 23.9 mg of Compound 33 as a white solid (with 98.8% ee). Analytical HPLC retention time and LC/MS are identical to its racemate, Compound 32C.

EXAMPLE 34

5-[(4-amino-1-piperidinyl)methyl]-N-[3-chloro-4-[(1-oxido-2-pyridinyl)methoxy]phenyl]pyrrolo[2,1-f][1,2,4]triazin-4-amine

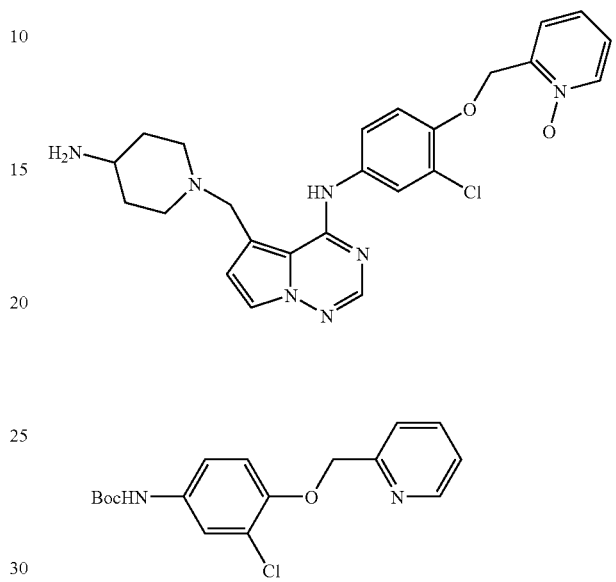

34A. To a stirred solution of 3-chloro-4-(pyridin-2-ylmethoxy)-phenylamine (220 mg, 0.93 mmoL) in 2.4 mL of THF was added di-t-butyl dicarbonate (245 mg, 1.12 mmoL) at room temperature. This reaction mixture was heated at 80° C. for 6 h and cooled to room temperature. The reaction mixture was concentrated in vacuo. The resultant product was diluted with 10 mL of DCM and concentrated in vacuo to give 289 mg of 3-chloro-4-(pyridin-2-ylmethoxy)-phenyl)-carbamic acid tert-butyl ester in 92% yield.

Analytical HPLC retention time=3.12 min. (YMC S5 ODS column 4.6×50 mm, 10–90% aqueous methanol over 4 minutes containing 0.2% phosphoric acid, 4 mL/min, monitoring at 220 nm) and a LC/MS M⁺+1=335.

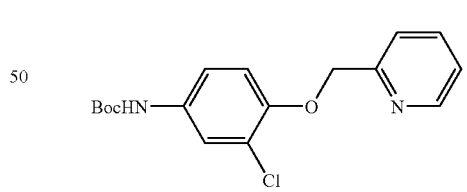

34B. To a stirred mixture of 3-chloro-4-(pyridin-2-ylmethoxy)-phenyl)-carbamic acid tert-butyl ester (280 mg, 0.84 mmoL) in 3.6 mL of DCM was treated MCPBA (269 mg, 1.09 mmoL). This mixture was stirred at room temperature for 2 h and then treated with 2.4 mL of TFA. The reaction mixture was stirred at room temperature for another 2 h and concentrated in vacuo. The residue was diluted with 25 mL of 1N NaOH solution and extracted with EtOAc (2×60 mL). The EtOAc extracts were dried (MgSO₄), filtered and concentrated in vacuo to give 201 mg of 2-(4-amino-2-chloro-phenoxymethyl)-pyridin-1-ol in 96% yield.

Analytical HPLC retention time=1.16 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=251

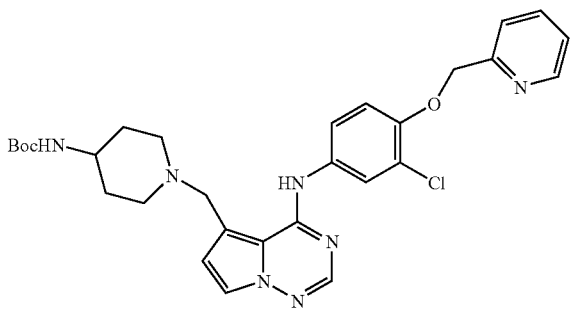

34C. A mixture of 1E (142 mg, 0.41 mmol) and 2-(4-amino-2-chloro-phenoxymethyl)-pyridin-1-ol (102 mg, 0.41 mmol) in DMA (1 ml) was heated at 70° C. for 4 h. The mixture was cooled to rt. The cooled mixture was added dropwise to a stirred solution of piperidin-4-yl-carbamic acid tert-butyl ester (122 mg, 0.61 mmol) and DIEA (0.21 ml, 1.23 mmol) in DMA (1 ml) at 70° C. under N$_2$ over 30 min. The resulting mixture was stirred for 3 h, cooled to rt, diluted with EtOAc (100 ml) and washed with water (6×80 ml). The EtOAc layer was then washed with brine (1×40 ml), dried (MgSO$_4$), filtered and concentrated in vacuo to give the boc product (132 mg, 55%). Analytical HPLC retention time=2.69 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=580.

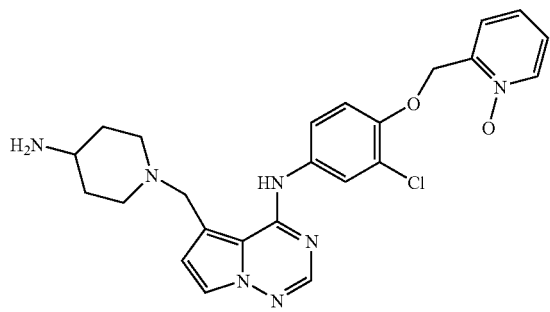

34D. To a solution of the boc (130 mg, 0.22 mmol) in CH$_2$Cl$_2$ (1.2 ml) was added TFA (2.4 ml). The mixture was stirred for 20 min, then concentrated in vacuo. The residue was purified by a Shimadzu auto prep HPLC, employing 0% to 100% 10 min gradient elution with 0.1%TFA in MeOH-water solvent system, 220 nM detection, 20 mL/min elution with a YMC ODS S5 20×100 mm column to give the desired product (79 mg, 73%). Analytical HPLC retention time=1.73 min. (YMC S5 ODS column 4.6×50 mm, 10–90% aqueous methanol over 4 minutes containing 0.2% phosphoric acid, 4 mL/min, monitoring at 220 nm) and a LC/MS M$^+$+1=480.

The following compounds are similarly prepared.

| Ex. No | Ar | Compound name | HPLC time (min) | (M + H)$^+$ |
|---|---|---|---|---|
| 35 | | | 1.82 | 494.7 |
| 36 | | | 1.61 | 480.7 |

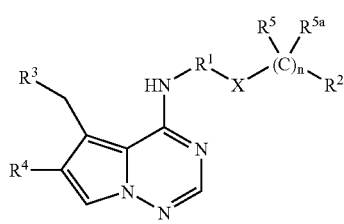

We claim:
1. A compound of formula I

$$\text{(I)}$$

wherein the symbols have the following meanings and are, for each occurrence, independently selected:
  $R^1$ and $R^2$ are independently aryl, substituted aryl, heteroaryl, substituted heteroaryl, heterocyclo or substituted heterocyclo;
  $R^3$ and $R^4$ are independently hydrogen, alkyl, substituted alkyl, halogen, alkoxy, substituted alkoxy, aryl, substituted aryl, heteroaryl, substituted heteroaryl, heterocyclo, substituted heterocyclo, alkylheterocyclo, substituted alkylheterocyclo, —O-heterocyclo or —NHCOOalkylheterocyclo;
  $R^5$ and $R^{5a}$ are hydrogen, alkyl, substituted alkyl or halogen,
  X is —O— or $NR^5$;
  n is 1 or 2;
  or a pharmaceutically acceptable salt or stereoisomer thereof.
2. The compound as defined in claim 1 wherein
  X is —O—;
  $R^1$ and $R^2$ are independently aryl, substituted aryl, heteroaryl or substituted heteroaryl; and
  $R^5$ and $R^{5a}$ are hydrogen or lower alkyl;
  or a pharmaceutically acceptable salt or stereoisomer thereof.
3. The compound as defined in claim 2 wherein
  $R^1$ and $R^2$ are independently phenyl, substituted phenyl, heteroaryl or substituted heteroaryl.
4. The compound as defined in claim 1 wherein
  X is —O—;
  $R^1$ is phenyl, substituted phenyl, pyridine or substituted pyridine; and R² is phenyl, substituted phenyl, pyrazine, substituted pyrazine, pyridine or substituted pyridine.

5. The compound according to claim 1 selected from the group consisting of

[5-(4-Amino-piperidin-1-ylmethyl)-pyrrolo[2,1-f][1,2,4]triazin-4-yl]-[3-chloro-4-(pyridin-2-ylmethoxy)-phenyl]-amine;

[5-(4-Amino-piperidin-1-ylmethyl)-pyrrolo[2,1-f][1,2,4]triazin-4-yl]-[3-chloro-4-(pyridin-3-ylmethoxy)-phenyl]-amine;

[5-(4-Amino-piperidin-1-ylmethyl)-pyrrolo[2,1-f][1,2,4]triazin-4-yl]-[3-chloro-4-(3-fluoro-benzyloxy)-phenyl]-amine;

5-[[5-[(4-Amino-1-piperidinyl)methyl]pyrrolo[2,1-f][1,2,4]triazin-4-yl]amino]-2-[(3-fluorophenyl)methoxy]benzonitrile;

5-[(4-Amino-1-piperidinyl)methyl]-N-[3-chloro-4-(pyrazinylmethoxy)-phenyl]pyrrolo[2,1-f][1,2,4]triazin-4-amine;

5-[[(3R,4S)-rel-4-Amino-3-methyl-1-piperidinyl]methyl]-N-[3-chloro-4-(2-pyridinylmethoxy)phenyl]pyrrolo[2,1-f][1,2,4]triazin-4-amine;

5-[(4-Amino-1-piperidinyl)methyl]-N-[3-chloro-4-[(1-oxido-2-pyridinyl)methoxy]phenyl]pyrrolo[2,1-f][1,2,4]triazin-4-amine, and trans-4-Amino-1-{4-[3-chloro-4-(pyridin-2-ylmethoxy)-phenylamino]-pyrrolo[2,1-f][1,2,4]triazin-5-yl-methyl}-piperidin-3-ol.

6. A pharmaceutical composition comprising at least one compound of claim 1 and a pharmaceutically acceptable carrier therefor.

* * * * *